(12) United States Patent
Ten Kate

(10) Patent No.: US 9,835,644 B2
(45) Date of Patent: Dec. 5, 2017

(54) ESTIMATING VELOCITY IN A HORIZONTAL OR VERTICAL DIRECTION FROM ACCELERATION MEASUREMENTS

(75) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 773 days.

(21) Appl. No.: 14/236,392

(22) PCT Filed: Aug. 17, 2012

(86) PCT No.: PCT/IB2012/054192
§ 371 (c)(1),
(2), (4) Date: Jan. 31, 2014

(87) PCT Pub. No.: WO2013/024461
PCT Pub. Date: Feb. 21, 2013

(65) Prior Publication Data
US 2014/0156216 A1    Jun. 5, 2014

Related U.S. Application Data

(60) Provisional application No. 61/524,813, filed on Aug. 18, 2011.

(51) Int. Cl.
*G01P 7/00* (2006.01)
*A61B 5/11* (2006.01)
(Continued)

(52) U.S. Cl.
CPC .............. *G01P 7/00* (2013.01); *A61B 5/1117* (2013.01); *A61B 5/7225* (2013.01); *G01P 15/00* (2013.01);
(Continued)

(58) Field of Classification Search
CPC .... G01C 21/165; G01C 21/16; G01C 21/206; G06F 3/0346
See application file for complete search history.

(56) References Cited

U.S. PATENT DOCUMENTS 7,489,298 B2 *   2/2009   Liberty ................. G06F 1/3215
                                                                345/156
2009/0048540 A1   2/2009   Otto et al.
(Continued)

FOREIGN PATENT DOCUMENTS

CN      102023233 A    4/2011
EP        1195139      4/2002
(Continued)

OTHER PUBLICATIONS

G. Anania et al., "Development of a Novel Algorithm of r Human Fall Detection Using Wearable Sensors", IEEE Sensors May 2008, Conference, pp. 1336-1339.
(Continued)

*Primary Examiner* — Elias Desta

(57) ABSTRACT

There is provided a method of determining an estimate of the velocity of a device in a horizontal or vertical direction, the method comprising obtaining measurements of the acceleration acting on the device in three dimensions; using a first filter and the obtained measurements to estimate acceleration due to gravity; estimating the acceleration acting in a horizontal or vertical direction due to motion of the device using the estimated acceleration due to gravity; integrating the estimate of the acceleration acting in said direction due to motion of the device to give an estimate of velocity in said direction; and using a second filter to remove offset and/or drift from the velocity to give a filtered velocity; wherein at least one of the first filter and second filter is a non-linear
(Continued)

filter. An apparatus configured to operate according to the above method is also provided.

15 Claims, 15 Drawing Sheets

(51) Int. Cl.
    *G08B 21/04*     (2006.01)
    *G01P 15/00*     (2006.01)
    *A61B 5/00*     (2006.01)

(52) U.S. Cl.
    CPC ....... *G08B 21/043* (2013.01); *G08B 21/0446* (2013.01); *A61B 5/0002* (2013.01); *A61B 2562/0219* (2013.01)

(56) References Cited

U.S. PATENT DOCUMENTS

2009/0278798 A1* 11/2009 Kim ................... G06F 3/011 345/158
2010/0121226 A1   5/2010  Ten Kate et al.
2011/0060543 A1   3/2011  Franke et al.
2011/0066377 A1   3/2011  Takaoka

FOREIGN PATENT DOCUMENTS

| EP | 1832881 | 9/2007 |
|---|---|---|
| JP | H0961445 A | 3/1997 |
| JP | H10332418 A | 12/1998 |
| JP | 2010038839 | 2/2010 |
| WO | WO2004114245 | 12/2004 |
| WO | 2007021766 A2 | 2/2007 |
| WO | WO2009101566 | 8/2009 |
| WO | 2010035191 A2 | 4/2010 |
| WO | WO2010037564 | 4/2010 |
| WO | WO2011064705 | 6/2011 |

OTHER PUBLICATIONS

H.J. Luinge et al., "Inclination Measurement of Human movement Using a 3-D Accelerometer With Autocalibration", IEEE Transactions on neural systems and Rehabilitation Engineering, vol. 12, No. 1, Mar. 2004, pp. 112-121.

J.T. Perry et al., "Survey and Evaluation of Real-Time Fall Detection Approaches", IEEE, Jun. 2009, pp. 158-164.

Degen et al, "Speedy: A Fall Detector in a Wrsit Watch", ISWC, 2003, pp. 1-4.

Kangas et al, "Comparison of Low-Complexity Fall Detection Algorithms for Body Attached Accelerometers", Gait & Posture, vol. 28, 2008, p. 285-291.

Bourke et al, "Fall-Detection Through Vertical Velocity Thresholding Using a Tri-Axial Accelerometer Characterized Using an Optical Motion-Capture System", 30th Annual International IEEE EMBS Conference, 2008, pp. 2832-2835.

Bourke, "Evaluation of Waist-Mounted Tri-Axial Accelerometer Based Fall-Detection Algorithms During Scripted and Continuous Unscripted Activites", Journal of Biomechanics, vol. 43, 2010, pp. 3051-3057.

\* cited by examiner

ESTIMATING VELOCITY IN A HORIZONTAL OR VERTICAL DIRECTION FROM ACCELERATION MEASUREMENTS

CROSS-REFERENCE TO PRIOR APPLICATIONS

This application is the U.S. National Phase application under 35 U.S.C. §371 of International Application Serial No. PCT/IB2012/054192, filed on Aug. 17, 2012, which claims the benefit of U.S. Provisional Application Ser. No. 61/524,813, filed on Aug. 18, 2011. These applications are hereby incorporated by reference herein.

TECHNICAL FIELD OF THE INVENTION

The invention relates to a method and apparatus for measuring or estimating the velocity of a device in a horizontal or vertical direction based on measurements of the acceleration experienced by the device. The invention also relates to a method and apparatus for measuring or estimating the height or a change in the height of a device from the estimated vertical velocity, or for estimating the horizontal position or displacement from the estimated horizontal velocity.

BACKGROUND TO THE INVENTION

Falling is a significant problem in the care of the elderly that can lead to morbidity and mortality. From a physical perspective, falls cause injuries, while from the mental perspective, falls cause fear-of-falling, which in turn leads to social isolation and depression.

Fall detection devices and systems are available that can provide an automated and reliable means for detecting when a user has fallen. If a fall is detected, the device or system issues an alarm which summons help to the user. This assures the user that adequate measures will be taken in the event that a fall occurs.

Commonly, fall detectors are based on an accelerometer (usually a 3D accelerometer that measures acceleration in three dimensions) that is part of a device to be attached to the user's body. The signals from the accelerometer are processed to determine whether a fall has taken place.

The reliability of fall detection can be improved by making use of further sensors which can be used to detect various different features that are characteristic of a fall. Important features include the impact of the user with the ground during the fall, an orientation change as the user falls, and a reduction in the height of the sensor unit above the ground. In EP 1642248, the use of an air pressure sensor is proposed to detect a change in the relative height measured by the device.

Currently available air pressure sensors provide a resolution in the relative altitude of the order of 10 cm. However, the nature of these pressure sensors means that their measurements are sensitive to gravity, and hence to the orientation of the sensor unit. This can be addressed by compensating the pressure sensor measurements for the orientation of the sensor unit, as described in WO 2009/101566. In addition, air pressure sensors clearly also respond to barometric fluctuations in the environment, and therefore the fall detector needs to verify whether the height change suggested by an increase in air pressure measurements is due (or can be due) to the motion of the sensor unit and the user. A further problem with air pressure sensors is that they increase the complexity of the mechanical construction of the device that houses the sensors. In particular, the device is required to have a fast-responding channel between the air pressure sensor inside the device and the environmental air outside, with this channel also being shielded against moisture, light, and other pollution.

Another approach to determining a measurement for the change in height is to use the accelerometer signal. By integrating the vertical acceleration signal, a measure for vertical velocity can be obtained, and by integrating the vertical velocity signal, a measure for position/height can be obtained. The integration typically requires knowledge of the initial vertical velocity and initial position/height.

Since in fall detection one aim is to detect a change in height, i.e. a difference between two positions in time, the integration can in fact be performed without knowledge of the value of the initial position, since it cancels in the difference equation.

In addition, in fall detection, the initial vertical velocity is zero, provided the "initial" time moment is correctly chosen. In common daily situations, this can be any point before the onset of the fall. It will be noted, however, that any deviation from zero of the true, physical vertical velocity integrates over the chosen range to an error in the position/height estimation.

However, another problem in using double integration of an accelerometer signal concerns the proper separation of the acceleration due to gravity from the component of acceleration due to the motion of the user. To achieve a precision in height measurement of 10 cm over 1 second, the residual gravity component in the acceleration signal should stay within 0.2 $ms^{-2}$. Given that gravity is approximately 10 $ms^{-2}$, gravity needs to be separated with an accuracy of a few percent.

Since the orientation of the sensor unit is likely to be changing as the user falls, the direction of the vertical in terms of the coordinate system of the sensor unit will be changing as well. Here, the same problem arises. An error in the orientation estimation causes an error in the computation of the non-gravitational vertical component of acceleration. For the same reason, an error in the orientation also implies an error in the calculation of the corresponding gravity component. These errors manifest themselves in the vertical velocity estimate and therefore also in the estimated height (or change in height) of the device.

Furthermore, if the acceleration sensor is not properly calibrated, or has lost calibration over time, the sensed gravity will also change with the orientation of the sensor unit.

Therefore, there is a need for an improved method and apparatus for measuring or estimating the velocity of a device in a horizontal or vertical direction based on measurements of the acceleration experienced by the device that overcomes the above problems.

SUMMARY OF THE INVENTION

According to a first aspect of the invention, there is provided a method of determining an estimate of the velocity of a device in a horizontal or vertical direction, the method comprising obtaining measurements of the acceleration acting on the device in three dimensions; using a first filter and the obtained measurements to estimate acceleration due to gravity; estimating the acceleration acting in a horizontal or vertical direction due to motion of the device using the estimated acceleration due to gravity; integrating the estimate of the acceleration acting in said direction due to motion of the device to give an estimate of the velocity in said direction; and using a second filter to remove offset and/or drift from the velocity to give a filtered velocity; wherein at least one of the first filter and second filter is a non-linear filter.

In one embodiment, the step of using a first filter and the obtained measurements to estimate acceleration due to gravity comprises estimating the acceleration acting in a vertical direction on the device from the obtained measurements; and applying the first filter to the estimate of the acceleration acting in a vertical direction to estimate the acceleration due to gravity; wherein the step of estimating the acceleration comprises estimating the acceleration acting in a vertical direction due to motion of the device; and wherein the step of estimating the acceleration acting in a vertical direction due to motion of the device using the estimated acceleration due to gravity comprises subtracting the estimated acceleration due to gravity from the estimated acceleration acting in a vertical direction to give the estimate of the acceleration acting in a vertical direction due to motion of the device.

In that embodiment, the step of estimating the acceleration acting in a vertical direction on the device from the obtained measurements can comprise computing the norm of the obtained measurements.

In an alternative embodiment, the step of using a first filter and the obtained measurements to estimate acceleration due to gravity comprises applying the first filter to the obtained measurements to estimate the acceleration due to gravity in three dimensions; and wherein the step of estimating the acceleration acting in a horizontal or vertical direction due to motion of the device using the estimated acceleration due to gravity comprises using the estimated acceleration due to gravity to estimate the acceleration acting in a horizontal or vertical direction from the obtained measurements; and subtracting the estimated acceleration due to gravity from the estimated acceleration acting in said direction to give the estimate of the acceleration acting in said direction due to motion of the device.

In one embodiment, the second filter is a non-linear filter and the first filter is a linear filter. In an alternative embodiment, the first filter is a non-linear filter and the second filter is a linear filter.

The non-linear filter can, for example, be selected from a median filter, a weighted median filter, a recursive median filter, a subMedian filter, an adaptive median filter and a mode filter. The linear filter can, for example, be selected from an estimator that outputs a constant value, a low-pass filter and a moving average filter.

In a preferred embodiment, both the first filter and the second filter are non-linear filters. The non-linear filters can, for example, each be selected from a median filter, a weighted median filter, a recursive median filter, a subMedian filter, an adaptive median filter and a mode filter.

According to a preferred embodiment of the invention, the operation of the first filter comprises downsampling an input signal; and applying a non-linear filter to the downsampled signal.

Preferably, the step of downsampling comprises generating a plurality of downsampled signals, each having a respective phase; and wherein the step of applying the non-linear filter comprises applying the non-linear filter to each of the plurality of downsampled signals.

In one embodiment, the operation of the first filter further comprises combining the plurality of filtered signals into a single signal; and upsampling the single signal to the original sampling rate.

In an alternative embodiment, the operation of the first filter further comprises upsampling each of the plurality of filtered signals; and combining the plurality of upsampled filtered signals into a single signal.

In a preferred embodiment, the operation of the first filter further comprises prior to the step of downsampling, applying a low-pass filter to the input signal to produce a low-pass filtered signal; wherein the step of downsampling comprises downsampling the low-pass filtered signal to a rate based on the cut-off frequency of the low-pass filter.

According to a preferred embodiment of the invention, the operation of the second filter comprises computing the median value in each of a plurality of subwindows centered at or near a sample of interest in an input signal; and adapting the window size of a median filter used to generate an output value for the sample of interest based on the computed median values; wherein the window size that is used to generate the output value is larger than that of the subwindow centered on the sample of interest if the median value of the subwindow centered on the sample of interest is the maximum or minimum of the plurality of median values.

In one embodiment, if the median value of the subwindow centered on the sample of interest is not the maximum or minimum of the plurality of median values, the value determined for the sample preceding the sample of interest is used as the output value.

According to an alternative embodiment of the invention, the operation of the second filter comprises computing the median value in each of a plurality of subwindows centered at or near a sample of interest in an input signal; and adapting the window size of a median filter used to generate an output value for the sample of interest based on the computed median values, wherein the window size is adapted as follows:
    if the median value of the subwindow centered on the sample of interest is the maximum of the median values, using a window size that is larger than that of the subwindow centre centered on the sample of interest to generate an output value;
    if the median value of the subwindow centered on the sample of interest is the minimum of the median values, using a window size that is the same as that of the subwindow centered on the sample of interest to generate an output value;
    otherwise, using a window that corresponds to the subwindow centered on the sample of interest and the subwindow that has the maximum of the median values to generate an output value.

This aspect of the invention also provides a method of estimating the position or height of a device, the method comprising determining an estimate of the velocity of a device in a horizontal or vertical direction as described above; and integrating the filtered velocity to give estimates of the position or height of the device.

Another aspect of the invention provides a method of detecting a fall by a user of a device, the method comprising estimating the height of the device as described in the preceding paragraph; and detecting a fall by examining changes in the estimated height of the device over time.

A method of estimating the horizontal displacement or change in height of a device is also provided that comprises determining an estimate of the velocity of a device in a horizontal or vertical direction as described above; and summing the filtered velocity estimates in a time window over which the change in height is to be calculated.

Another aspect of the invention provides a method of detecting a fall by a user of a device, the method comprising estimating the change in height of the device as described in the preceding paragraph; and detecting a fall by examining the estimated changes in the height of the device.

In some embodiments, after detecting a fall, the method further comprises examining changes in the height of the device to detect an increase in the height of the device corresponding to the user getting up.

According to another aspect of the invention, there is provided a computer program product, comprising a computer readable medium having computer program code embodied therein, the computer program code being configured such that, upon execution by a computer or processor, the computer or processor performs the method as defined in any of the above paragraphs.

According to a further aspect of the invention, there is provided an apparatus, comprising processing means that is configured to receive measurements of the acceleration acting on a device in three-dimensions, use a first filter and the measurements of the acceleration to estimate acceleration due to gravity; estimate the acceleration acting in a horizontal or vertical direction due to motion of the device using the estimated acceleration due to gravity; integrate the estimate of the acceleration acting in said direction due to motion of the device to give an estimate of velocity in said direction; and use a second filter to remove offset and/or drift from the velocity to give a filtered velocity; wherein at least one of the first filter and second filter used by the processing means is a non-linear filter.

In one embodiment, the processing means is configured to use a first filter and the measurements of the acceleration to estimate acceleration due to gravity by estimating the acceleration acting in a vertical direction on the device from the measurements of the acceleration; and applying the first filter to the estimate of the acceleration acting in a vertical direction to estimate the acceleration due to gravity; wherein the step of estimating the acceleration comprises estimating the acceleration acting in a vertical direction due to motion of the device; and wherein the processing means is configured to estimate the acceleration acting in a vertical direction due to motion of the device using the estimated acceleration due to gravity by subtracting the estimated acceleration due to gravity from the estimated acceleration acting in a vertical direction to give the estimate of the acceleration acting in a vertical direction due to motion of the device.

In this embodiment, the processing means may be configured to estimate the acceleration acting in a vertical direction on the device from the received measurements by computing the norm of the received measurements.

In an alternative embodiment, the processing means is configured to use a first filter and the measurements of the acceleration to estimate acceleration due to gravity by applying the first filter to the measurements of the acceleration to estimate the acceleration due to gravity in three dimensions; and wherein the processing means is configured to estimate the acceleration acting in a horizontal or vertical direction due to motion of the device using the estimated acceleration due to gravity by: using the estimated acceleration due to gravity to estimate the acceleration acting in said direction from the measurements of the acceleration; and subtracting the estimated acceleration due to gravity from the estimated acceleration acting in said direction to give the estimate of the acceleration acting in said direction due to motion of the device.

In one embodiment, the second filter is a non-linear filter and the first filter is a linear filter. In an alternative embodiment, the first filter is a non-linear filter and the second filter is a linear filter.

Preferably, the non-linear filter is selected from, for example, a median filter, a weighted median filter, a recursive median filter, a subMedian filter, an adaptive median filter and a mode filter, and the linear filter is selected from, for example, an estimator that outputs a constant value, a low-pass filter and a moving average filter.

In a preferred embodiment, both the first filter and the second filter are non-linear filters. The non-linear filters can, for example, each be selected from a median filter, a weighted median filter, a recursive median filter, a subMedian filter, an adaptive median filter and a mode filter.

According to a preferred embodiment of the invention, the first filter used by the processing means is configured to downsample an input signal and apply a non-linear filter to the downsampled signal.

Preferably, the first filter is configured to downsample the input signal to generate a plurality of downsampled signals, each having a respective phase; and wherein the first filter is configured to apply a non-linear filter to each of the plurality of downsampled signals.

In one embodiment, the first filter is further configured to combine the plurality of filtered signals into a single signal; and upsample the single signal to the original sampling rate.

In an alternative embodiment, the first filter is further configured to upsample each of the plurality of filtered signals; and combine the plurality of upsampled filtered signals into a single signal.

In a preferred embodiment, the first filter is further configured to, prior to downsampling, apply a low-pass filter to the input signal to produce a low-pass filtered signal; wherein the first filter is configured to downsample the low-pass filtered signal to a rate based on the cut-off frequency of the low-pass filter.

According to a preferred embodiment of the invention, the second filter used by the processing means is configured to compute the median value in each of a plurality of subwindows centered at or near a sample of interest in an input signal; and adapt the window size of a median filter used to generate an output value for the sample of interest based on the computed median values, wherein
if the median value of the subwindow centered on the sample of interest is the maximum or minimum of the plurality of median values, a window size is used to generate an output value that is larger than that of the subwindow centered on the sample of interest.

In one embodiment, if the median value of the subwindow centered on the sample of interest is not the maximum or minimum of the plurality of median values, the second filter is configured to use the value determined for the sample preceding the sample of interest is used as the output value.

According to an alternative embodiment of the invention, the second filter used by the processing means is configured to compute the median value in each of a plurality of subwindows centered at or near a sample of interest in an input signal; and adapt the window size of a median filter used to generate an output value for the sample of interest based on the computed median values, wherein the window size is adapted as follows:
if the median value of the subwindow centered on the sample of interest is the maximum of the median values, using a window size that is larger than that of the subwindow centre centered on the sample of interest to generate an output value;
if the median value of the subwindow centered on the sample of interest is the minimum of the median values, using a window size that is the same as that of the subwindow centered on the sample of interest to generate an output value;

otherwise, using a window that corresponds to the subwindow centered on the sample of interest and the subwindow that has the maximum of the median values to generate an output value.

In a further embodiment, the processing means is further configured to estimate the horizontal position or height of a device from the filtered velocity by integrating the filtered velocity to give the position or height of the device.

In another embodiment, the processing means is further configured to estimate the horizontal displacement or change in height of the device by summing the filtered velocity estimates in a time window over which the displacement or change in height is to be calculated.

In a preferred embodiment the apparatus is for use in detecting falls by a user of a device, and wherein the processing means is further configured to detect a fall by examining changes in the estimated height of the device over time.

In another preferred embodiment, the apparatus is for use in detecting falls by a user of a device, and wherein the processing means is further configured to detect a fall by examining the estimated changes in the height of the device.

In a further embodiment the processing means is further configured to, after detecting a fall, examine changes in the height of the device to detect an increase in the height of the device corresponding to the user getting up.

According to another aspect of the invention, there is provided a device that is configured to be worn by a user, and the device comprises an accelerometer that measures the acceleration acting on the device in three-dimensions; and an apparatus as described above.

According to yet another aspect of the invention, there is provided a system that comprises a device that is configured to be worn by a user, the device comprising an accelerometer that measures the acceleration acting on the device in three-dimensions; and a base unit that is configured to communicate with the device. The base unit comprises an apparatus as described above for processing the measurements of acceleration received from the device.

According to another aspect of the invention, there is provided a filter for filtering a digital signal, the filter being configured to downsample an input signal and apply a non-linear filter to the downsampled signal.

Preferably, the filter is configured to downsample the input signal to generate a plurality of downsampled signals, each having a respective phase; and wherein the filter is configured to apply a non-linear filter to each of the plurality of downsampled signals.

In one embodiment, the filter is further configured to combine the plurality of filtered signals into a single signal; and upsample the single signal to the original sampling rate.

In an alternative embodiment, the filter is further configured to upsample each of the plurality of filtered signals; and combine the plurality of upsampled filtered signals into a single signal.

In a preferred embodiment, the filter is further configured to, prior to downsampling, apply a low-pass filter to the input signal to produce a low-pass filtered signal; wherein the filter is configured to downsample the low-pass filtered signal to a rate based on the cut-off frequency of the low-pass filter.

According to yet another aspect of the invention, there is provided a filter for filtering a digital signal, the filter being configured to compute the median value in each of a plurality of subwindows centered at or near a sample of interest in an input signal; and adapt the window size of a median filter used to generate an output value for the sample of interest based on the computed median values, wherein the window size that is used to generate the output value is larger than that of the subwindow centered on the sample of interest if the median value of the subwindow centered on the sample of interest is the maximum or minimum of the plurality of median values.

According to further aspects of the invention, there are provided methods of filtering a digital signal corresponding to the filters defined above.

BRIEF DESCRIPTION OF THE DRAWINGS

Particular embodiments of the invention will now be described, by way of example only, with reference to the following drawings, in which.

DETAILED DESCRIPTION OF PREFERRED EMBODIMENTS

The invention will be described below in terms of its use in detecting falls by a user (in which the estimated vertical velocity can optionally be used to give the height, or change in height, of a device worn by a user), it will be appreciated that the invention can be used in other applications, such as in monitoring the physical activity of users (for example calculating the energy expended or power exerted during activity, or calculating the type of activity such as walking, sitting, lying, and standing). In these applications, the horizontal or vertical velocity may be used directly and/or also further integrated to determine the displacement or height of the device worn by the user. In the description of the invention provided below, the estimation of vertical velocity and height is described in detail, but it will be appreciated by those skilled in the art that the described techniques can be used to determine the horizontal component of acceleration and therefore the horizontal velocity and horizontal position or displacement.

Furthermore, although in the fall detection application described below the height or changes in height of the device/user are estimated from acceleration measurements in order to determine if a fall has taken place, the estimated height of the device can also be used to determine whether the user is getting up after a fall (in which case a fall alarm can potentially be revoked), or the length of time that the user has been lying on the floor.

Figure 1A:
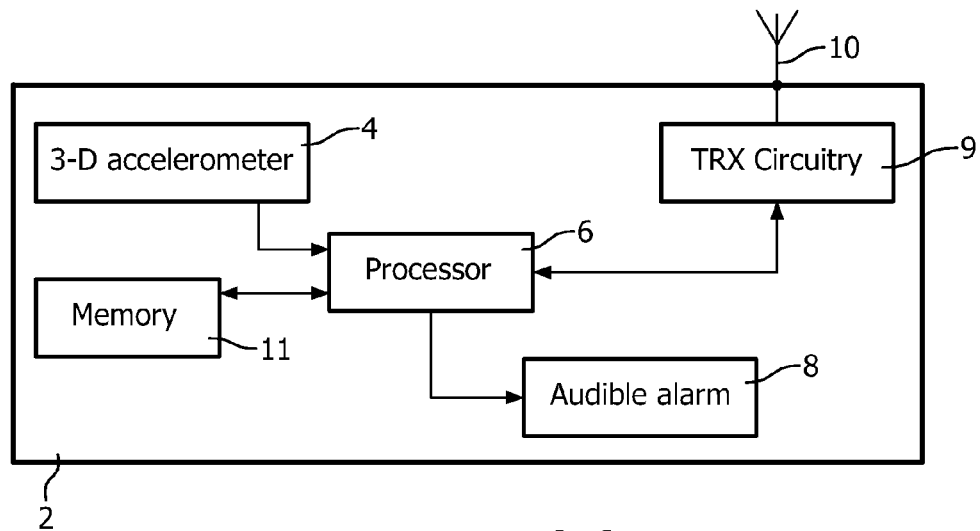
FIGS. 1(a) and (b) are block diagrams of a device and system in accordance with embodiments of the invention respectively.

FIG. 1(a) illustrates an exemplary device 2 that implements a method of determining vertical velocity in accordance with the invention for the purpose of fall detection. The device 2 is in the form of a sensor unit that is to be worn by a user. The device 2 can be provided in the form of a pendant with a neck cord for placement around the user's neck, but alternatively the device 2 can be configured to be worn at or on a different part of the user's body, such as the wrist, waist, trunk, pelvis or sternum, and will comprise a suitable arrangement for attaching the device 2 to that part of the body (for example a belt or a strap).

The device 2 is used to measure the accelerations experienced by the user and to process the measurements to determine the vertical velocity and then the change in height of the device 2 (and hence the change in height of the user). Although not described herein, it will be appreciated that a device 2 may perform additional processing on the acceleration measurements to identify other characteristics of a fall, such as an impact or a period of immobility following an impact. It will also be appreciated that the device 2 may contain further sensors, such as a gyroscope, magnetometer, air pressure sensor and/or air flow sensor, whose signals can be processed to determine, or to assist in determining, height, orientation or other characteristics associated with a fall.

The device 2 comprises an accelerometer 4 that measures acceleration along three orthogonal axes. The signals output by the accelerometer 4 are provided to a processor 6 for analysis. As illustrated, the device 2 comprises an audible alarm unit 8 that can be triggered by the processor 6 if a fall is detected. This alarm can summon help to the user. However, it will be appreciated that the presence of an audible alarm unit in the device 2 is optional. A further optional component is a help button that can be pressed by a user to summon help.

The device 2 further comprises transmitter or transceiver circuitry 9 and associated antenna 10 that can be used for transmitting the results of the processing to a remote (base) unit or for placing an emergency call to a call centre to summon help in the event that a fall is detected or in the event that a help button (if present) has been pressed.

The device 2 also optionally comprises a memory 11 that is used for storing measurements from the accelerometer 4, and for storing the results of the processing by the processor 6.

In some embodiments, the accelerometer 4 is a microelectromechanical system (MEMS) accelerometer.

The acceleration experienced by the accelerometer 4 can be sampled at a rate of 30 Hz, although it will be appreciated that many other sampling frequencies can be used (for example 50 Hz).

Figure 1B:
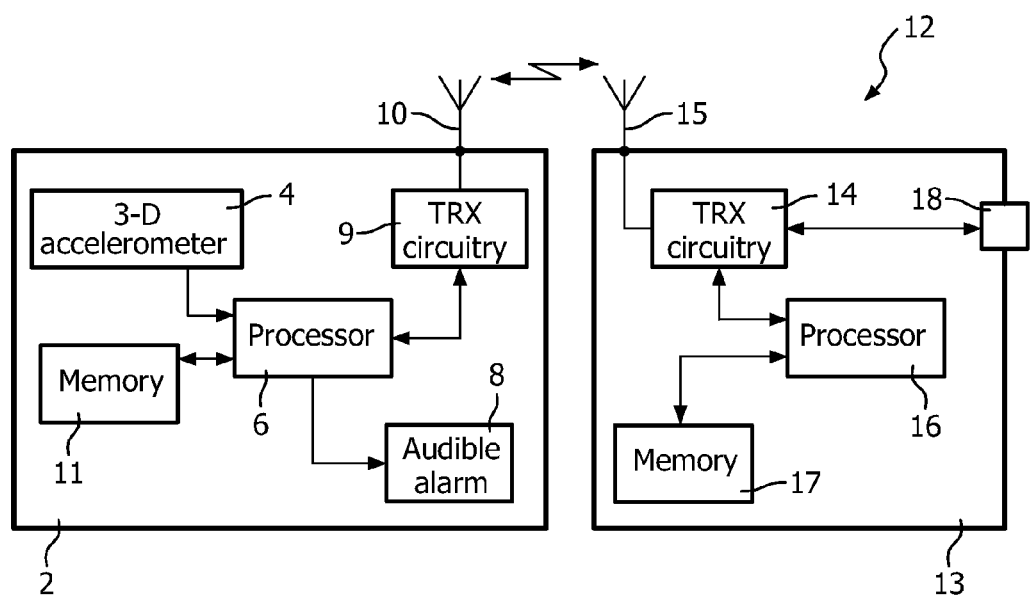

In an alternative embodiment of the invention, as illustrated in FIG. 1(b), the device 2 is part of a system 12 in which the processing of the accelerometer measurements can be performed in a base unit 13 that is separate to the device 2 worn by the user. In that case, the accelerometer measurements can be transmitted from the device/sensor unit 2 to the base unit 13 via the transceiver circuitry 9.

The base unit 13 comprises transceiver circuitry 14 and antenna 15 for receiving transmissions (such as the accelerometer measurements) from the device 2 and a processor 16 for processing the measurements according to the invention.

The base unit 13 also optionally comprises a memory 17 that is used for storing accelerometer measurements received from the device 2, and for storing the results of the processing by the processor 16.

The transceiver circuitry 14 may be configured for wirelessly placing an emergency call to a call centre, and/or may be configured for connection to a conventional PSTN line via port 18.

In a further alternative, the device 2 may perform some of the initial processing steps on the accelerometer measurements before transmitting the results to the base unit 13 which, for example, completes the processing and estimates the vertical velocity and change in height of the device 2.

It will be appreciated that only components of the device 2 (and system 12) that are required for explaining the invention have been illustrated in FIGS. 1(a) and (b), and a device 2 (or system 12) according to the invention may include further components and functionality to those described herein. For example, it will be appreciated that a device 2 (and base unit 13) will include some form of power source or supply and circuitry for controlling the operation of the device 2 (and base unit 13).

The following description of the invention refers to the device 2 shown in FIG. 1(a), but it will be readily appreciated by those skilled in the art how the invention can be adapted for use in the system 12 shown in FIG. 1(b).

Briefly, the method of determining an estimate of the velocity of a device in a vertical direction according to the illustrated embodiments of the invention comprises obtaining measurements of the acceleration acting in a vertical direction on the device 2 using the accelerometer 4, using a first filter to remove acceleration due to gravity from the obtained measurements to give an estimate of the acceleration acting in a vertical direction due to motion of the device 2, integrating the estimate of the acceleration acting in a vertical direction due to motion of the device to give an estimate of vertical velocity and using a second filter to remove offset and/or drift from the vertical velocity to give a filtered vertical velocity. According to the invention, one or both of the first filter and second filter is a non-linear filter.

Figure 2:
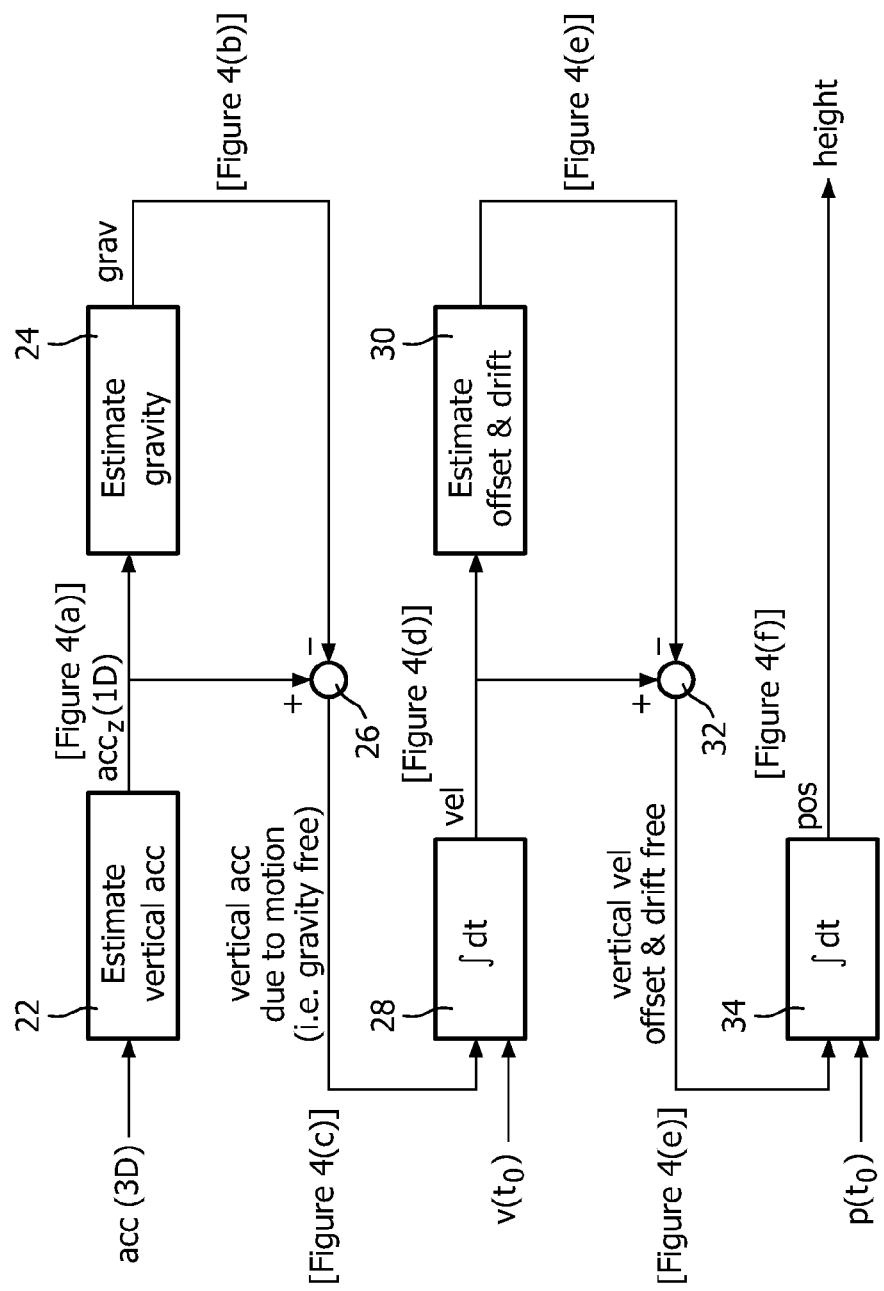
FIG. 2 is a block diagram illustrating the processing of an accelerometer signal to determine a height change in accordance with an embodiment of the invention.
Figure 3:
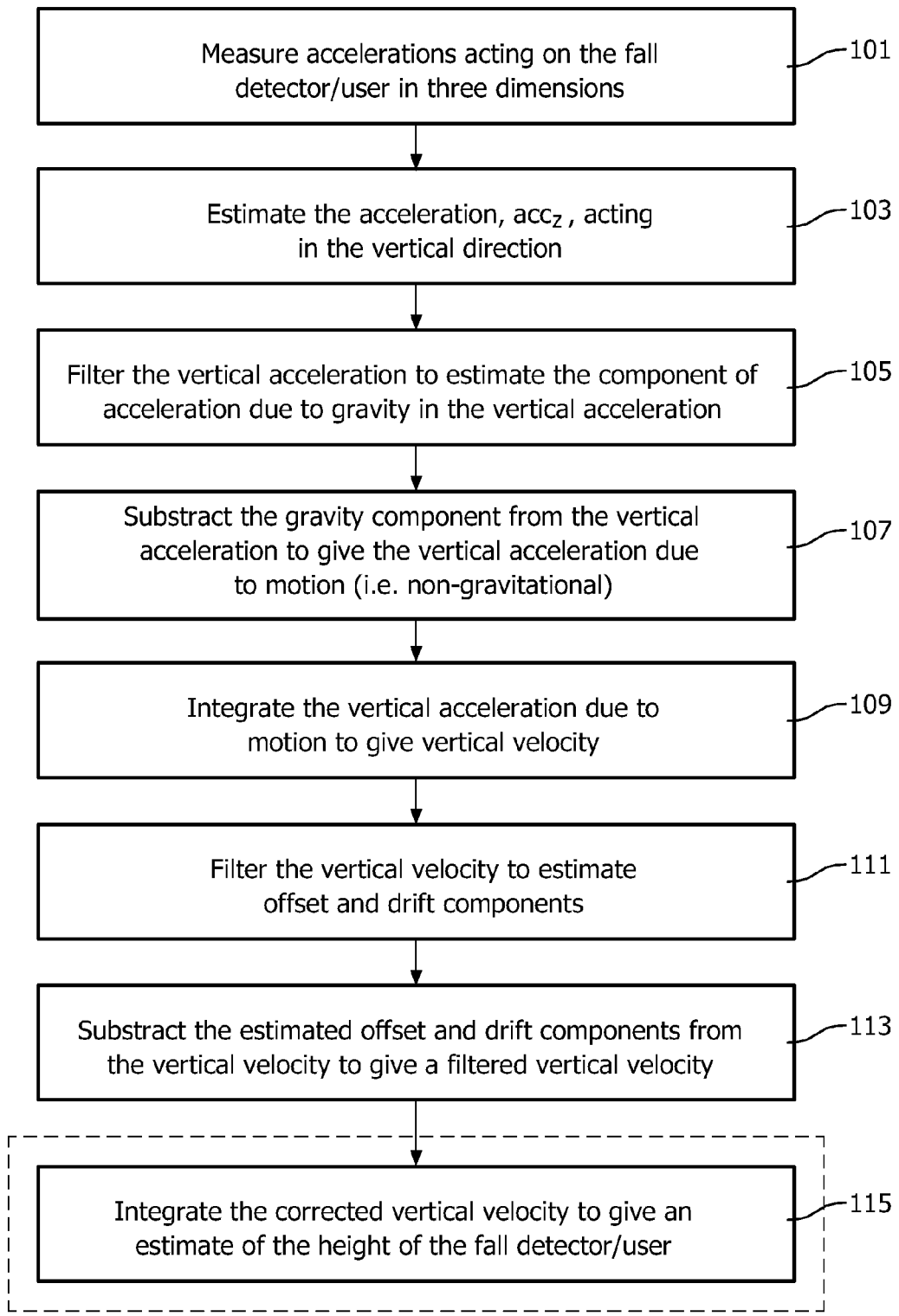
FIG. 3 is a flow chart illustrating a method of processing an accelerometer signal to determine a height change in accordance with an embodiment of the invention.

FIG. 2 shows a block diagram of the processing required to estimate the vertical velocity and then the change in height according to an embodiment of the invention. It will be appreciated by those skilled in the art that these processing blocks can be implemented within the processor 6 of the device 2 or as separate electronic components. A flow chart illustrating a corresponding method of estimating the vertical velocity is shown in FIG. 3 (steps 101-113), along with the further step (step 115) of estimating the height from the vertical velocity. FIGS. 4(a)-(f) are graphs illustrating the signals at various stages of the processing shown in FIG. 2.

As an initial step (step 101), a series of measurements of the acceleration acting on the accelerometer 4 (and therefore device 2) are collected. As indicated above, the accelerometer 4 measures acceleration in three dimensions and outputs a respective signal for each of the measurement axes.

The accelerometer measurements are provided to a first processing block 22 that processes the measurements to identify the component of acceleration acting in the vertical direction. This processing is represented in FIG. 3 by step 103, and can be performed in a number of different ways.

For an accurate estimation of the vertical acceleration to be made, it is desirable to obtain an accurate estimation of the orientation of the accelerometer 4 (and therefore device 2) so that a coordinate transformation (rotation) can be applied to the accelerometer measurements.

This orientation estimation can be obtained when the device 2 comprises a further sensor, such as a gyroscope and/or magnetometer, and the output from these sensors, possibly together with that from the accelerometer 4, is used to determine the coordinate transformation (rotation) to be applied to the accelerometer measurements. After coordinate transformation, the vertical component of acceleration can easily be identified.

Alternatively, acceleration due to gravity (which by definition acts in the vertical direction) can be estimated as the low-pass component of the accelerometer measurements (making sure that the magnitude of the low-pass component is constant), and the direction that this component acts can be used to determine the (vertical) orientation of the accelerometer 4. The acceleration in the direction of the low-pass filtered acceleration will correspond to the acceleration in the vertical direction. As a yet further alternative, the output of a process that is similar to that performed by processing block 24 when using a non-linear filter described below can be used to obtain an estimate of gravity and hence its direction (it is similar in the sense that it now operates on each of the components of the three-dimensional accelerometer signal).

A simpler way to estimate the vertical component of acceleration is to compute the norm of the 3D acceleration measurements. The signals output for each of the three measurement axes include gravity, which points in the vertical direction, and can be assumed to have a relatively large magnitude relative to accelerations due to motion. The accelerations due to motion and due to gravity combine as a vector sum. When computing the norm of this vector sum the contribution of the horizontal components are relatively small, since they are orthogonal to the gravity component and small in magnitude compared to this gravity component. Accelerations in the vertical direction will appear in the norm with an unaltered magnitude, provided that, when they are in a downward direction, they do not exceed gravity (otherwise the norm will turn the net negative component into a positive one, where an upward acceleration, such as by gravity alone, is defined positive). So, the norm is a cost-effective estimator of the vertical acceleration (including gravity). However, as suggested above, significant horizontal accelerations and large downward accelerations (i.e. exceeding gravity) will introduce distortions in the estimated vertical acceleration.

If the device 2 is implemented as, for example, a pendant to be worn around a user's neck, the device 2 will typically be in one particular orientation, and knowledge of this orientation can be used to identify the vertical component of acceleration from the accelerometer measurements. However, it will be appreciated that this approach is potentially subject to large errors if the device 2 is not worn properly or if its orientation changes during normal use or during a fall.

Another approach is described in WO 2010/035191 which describes a technique for estimating the vertical component of acceleration from a 3D accelerometer signal having an arbitrary orientation. According to that technique, the vertical component of acceleration is estimated by (i) examining the signals from the accelerometer to identify the axis of the accelerometer having the highest component of acceleration, (ii) determining the orientation of the accelerometer by determining the angle between the acceleration acting on the accelerometer (this acceleration being assumed to be generally due to gravity) and the axis with the highest component of acceleration and (iii) using the estimated orientation of the accelerometer to determine the acceleration in the vertical direction from the measurements of acceleration.

Figure 4A:
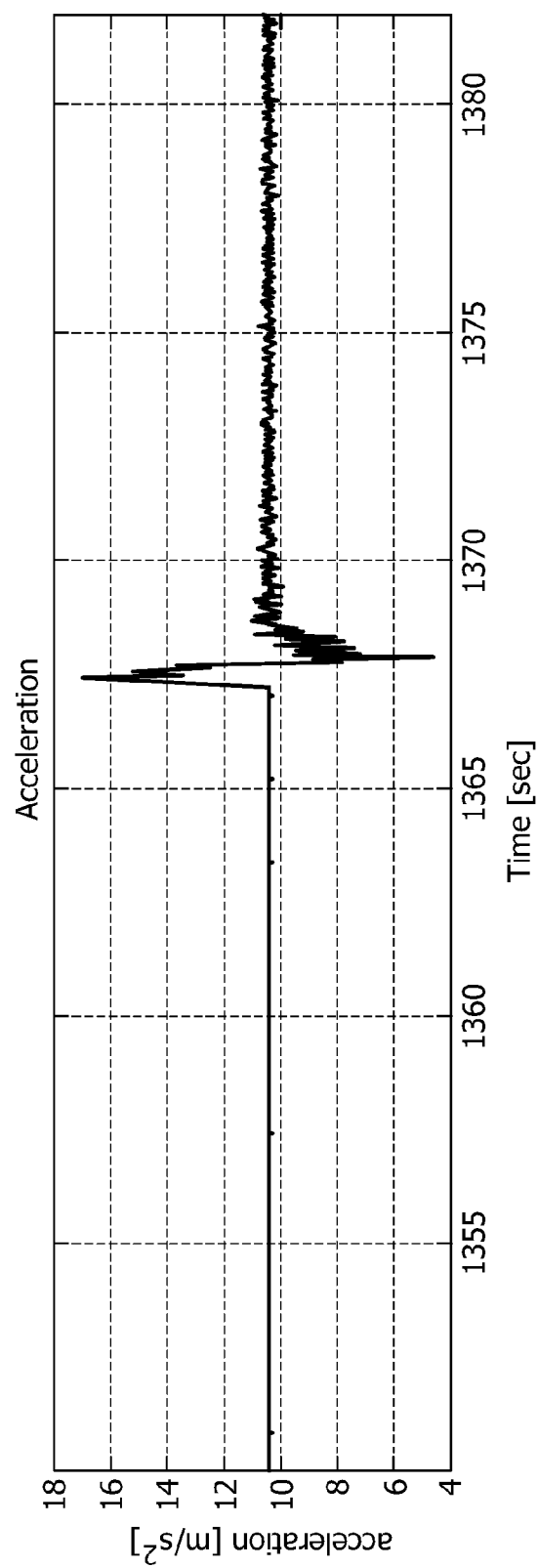
FIGS. 4(a) to 4(f) is a series of graphs showing the signals at various stages of the processing according to an embodiment of the invention.

The vertical component of acceleration output by the first processing block 22 is denoted $acc_z$ in FIG. 2, and an exemplary vertical component signal is shown in FIG. 4(a). This signal covers a period of time in which an increase in height occurs (around time 1368 seconds); where the device has been lifted from a stationary position on a desk and held in the hand, which induces some vibration. The vertical component of acceleration is provided to a second processing block 24 and to an addition/subtraction block 26.

Processing block 24 estimates the acceleration due to gravity in the vertical component of acceleration (corresponding to step 105 in FIG. 3) using a first filter.

In a simple embodiment, processing block 24 uses a constant value for gravity. This value may be 9.81 ms$^{-2}$, but it may be a different value, depending on the particular characteristics or calibration of the accelerometer 4. For example, it is not uncommon for an accelerometer 4 to output values for acceleration that are out from the actual values by 0.2 ms$^{-2}$ or more, and this can be factored in to the constant value used. This can be seen in FIG. 4(a) where the constant value is greater than 10 ms$^{-2}$. In this simple embodiment, processing block 24 can apply an estimator to the vertical component of acceleration that outputs a constant value for gravity (e.g. 9.81 ms$^{-2}$). As known, apart from the constant output, the estimator can be understood to be a filter.

In an alternative embodiment, processing block 24 can apply a linear filter to the vertical component of acceleration to provide the estimate for gravity. The linear filter can be a low-pass filter with an appropriate cut-off frequency. For example, the filter can be a moving average filter.

As known, a linear filter is characterized by its impulse response curve. A pulse at its input results in a signal that is spread in time. Therefore, a sudden change in acceleration, which happens during a fall, can be seen as a pulse superimposed on the continuously sensed gravity signal. Consequently, when estimating a gravitational component using a linear filter, there will be an over and under estimation due to the impulse spread. The severity of the over or under estimation depends on the bandwidth of the filter (or length of the impulse response). These over and under estimations will be treated in the subsequent integration step as part of the vertical acceleration due to motion and hence will lead to an erroneous velocity estimate, and thus position estimate too.

Furthermore, the component of gravity along each of the measurement axes of the accelerometer 4 changes when the orientation of the accelerometer 4 changes. This change appears as a transient error in the estimated gravity. The transient error is similar to the impulse response and has the same spread (more precisely, it is a step response). This spread also results in an error in the velocity and position estimate after the integration steps. This type of error is not present in the embodiment where the norm is used, assuming no calibration error, since the norm is insensitive of orientation.

Where the vertical component of acceleration is estimated (as in the process described above), this orientation change is taken into account, and the effect is reduced to the level of errors in the orientation estimated by block 22 (and in step 103). In the event that the measurements from the accelerometer 4 include an offset (e.g. the 0.2 ms$^{-2}$ mentioned above), the change in orientation will cause a change in magnitude of the sensed gravity component due to that offset. This is another effect that can cause transient errors, which again may appear as errors in the position estimate if not properly filtered.

Therefore, in view of these problems, in preferred embodiments of the invention, processing block 24 applies a non-linear filter to the vertical component of acceleration to provide an estimate for gravity. This is because a non-linear filter is much more capable of "ignoring" the sudden change in acceleration that occurs during a fall, or of following the transient that occurs upon a change in orientation.

In one preferred embodiment, the non-linear filter is a median filter. As known, a median filter processes each sample in the input signal in turn, replacing each sample with the median of a number of neighboring samples. The number of samples considered at each stage is determined by the window size of the filter. A typical half window size can be 1.6 seconds (so the window encompasses 1.6 seconds worth of samples before the current sample and 1.6 seconds worth of samples after the current sample).

A median filter is known for suppressing pepper-and-salt noise in video images, i.e. suppressing (black-and-white) signal spikes of short duration. The accelerations experienced during a fall can be considered as a spike in the acceleration signal of (relatively) short duration, and therefore removing this spike using a median filter will therefore produce a much better estimate of gravity, and does not suffer from the response spread problems associated with linear filters.

In another particularly preferred embodiment, the non-linear filter is a recursive median filter. This type of filter has the property that it tends to stick to its previous estimates (of gravity). In this way, a fluctuation in the acceleration does not immediately appear as crosstalk in the estimate of the gravity component, while a change, e.g. a step due to an orientation change and poor calibration of the accelerometer 4, is still followed.

As known, a recursive median filter is similar to a median filter, except that in computing the median for a particular sample it uses the already-computed median values in the sample window, rather than the original sample values in the signal.

The recursive median filter can be a forward or backward recursive median filter, which determines the direction in which the vertical acceleration signal is filtered.

The forward recursive median filter will try to keep the past values (i.e. keep them constant), while the backwards recursive median will try to keep the future values. Depending on the nature of the signal, the output of each of these types of recursive median filter can be different. For example, where the signal before a pulse has a lower value than after the pulse, a forward recursive median filter will tend to use the lower value, while the backwards recursive median filter will tend to use the higher value, and there will be a difference between the two outputs. Thus, it is possible to apply both filters separately to the vertical acceleration signal and average the results to obtain the gravity component. Alternatively linear interpolation between the points where the two filter outputs diverge can be used. Those skilled in the art will appreciate that it is possible to use other forms of combining the two results.

In an alternative embodiment, the non-linear filter is a weighted median filter, in which a respective weight is applied to each sample in the filter window.

In yet another alternative embodiment, the non-linear filter is a mode filter. This filter takes the sample value to which most of the sample values in the current window are closest.

In another embodiment, hybrid versions are used to filter the vertical acceleration. This filter estimates gravity and a decision process is run to decide what value to use. This decision can be to use a combination of estimates by different filters or to freeze the estimated gravity when the level of motion exceeds a threshold, for example.

In anther particularly preferred embodiment (although more complex than the use of a normal median filter or recursive median filter), a modified median filter, referred to herein as a subMedian filter, is used to filter the vertical acceleration. The subMedian filter is described in more detail below.

Figure 4B:
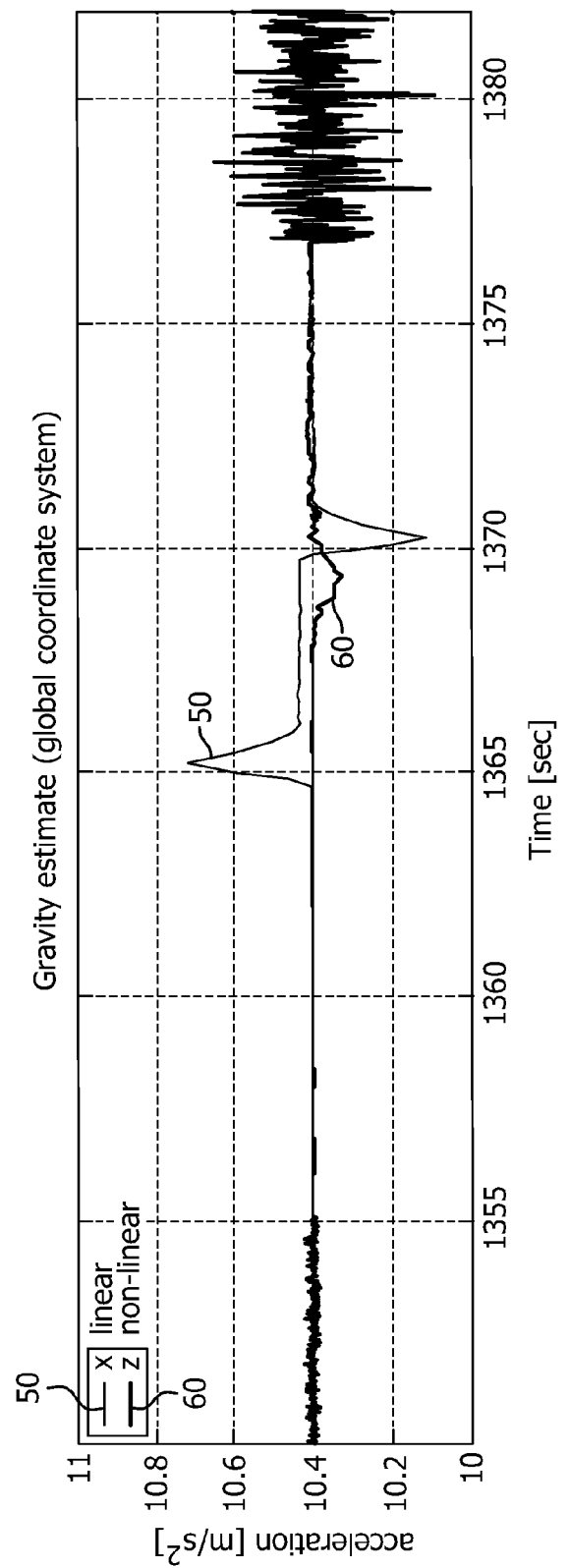

FIG. 4(b) shows the estimate of the acceleration due to gravity output by processing block 24 when a linear low-pass (moving average) filter is applied to the vertical acceleration signal (represented by line 50) and when a non-linear median filter is applied to the vertical acceleration signal (represented by line 60).

Although not illustrated in FIG. 2, it is possible to apply a further filter to the estimate of the gravitational acceleration to smooth the signal.

Where the device 2 is also configured to process the accelerometer measurements to determine if the user is getting up following a detected fall, it is possible to time-shift the estimated acceleration due to gravity by one or two seconds. When the user is lying on the floor, the signal for the gravitational component is relatively smooth (i.e. constant). Therefore, by time-shifting the gravitational estimate, a constant value can be used during the period where the user might be getting up.

Figure 4C:
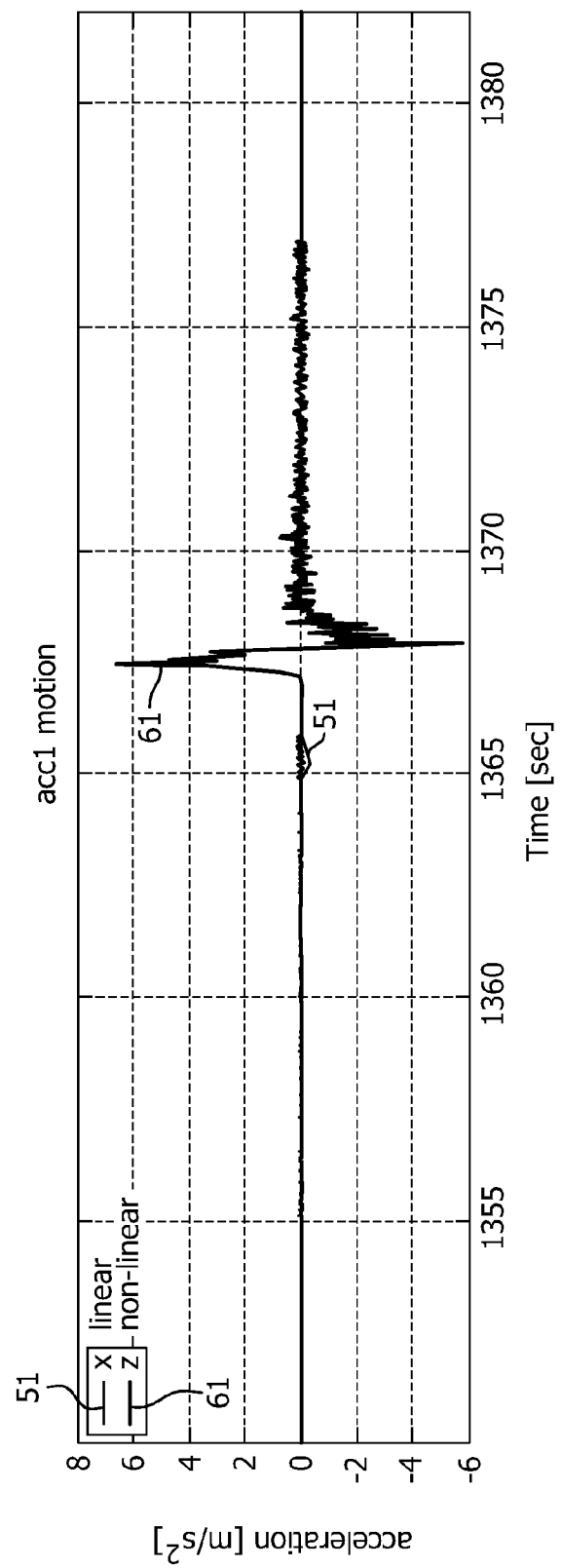

The estimate of the acceleration due to gravity output by processing block 24 is provided to the addition/subtraction block 26 where it is subtracted from the vertical component of acceleration output by the first processing block 22 to leave the acceleration in the vertical direction due to the motion of the device 2 (step 107). The estimated vertical acceleration due to motion output by block 26 (after subtracting the gravity estimate obtained using the non-linear median filter—labeled 61, and after subtracting the gravity estimate obtained using a moving average filter—labeled 51) is shown in FIG. 4(c).

It will be appreciated that the output of processing block 24 may be delayed with respect to the estimate of vertical acceleration provided directly to the addition/subtraction block 26 due to the time required for the processing by processing block 24. Therefore, the inputs to block 26 can be synchronized (for example by introducing a delay into the vertical acceleration estimate, $acc_z$).

It will also be appreciated that the non-linear median filter 24 that is applied to the vertical acceleration signal and the subsequent addition/subtraction block 26 can be replaced by a single filter, referred to herein as a 'complementary' median filter, which acts in the opposite way to the median filter, i.e. it passes the parts of the signal blocked by the median filter and blocks the parts of the signal passed by the median filter. Thus, the 'complementary' median filter passes the pulses of short duration representing the vertical acceleration due to motion of the device 2 and removes the gravitational acceleration in the vertical acceleration signal.

Referring to FIG. 3, this complementary filter would correspond to a combination of steps 105 and 107.

The signal representing the vertical acceleration due to the motion of the device 2 is then integrated with respect to time by processing block 28 to give an estimate of the velocity in the vertical direction (step 109). The initial velocity value $v(t_0)$ input to the integration block 28 is unknown, but is typically assumed to be zero. In any case, the next filtering stage (described further below) removes offset and drift in the vertical velocity signal, and therefore the initial velocity component (if non-zero) will be substantially removed.

It has been found that the gravity-free acceleration signal (shown in FIG. 4(c)), is not a perfect representation of the accelerations due to the physical movement of the device 2. The signal is distorted, effectively causing an additional velocity component in the output of the integration block 28. It has been assumed that the distortion is caused by the orientation estimation process performed by processing block 22. The distortion is not constant, but relates to the movement signal, and therefore cannot be filtered as part of the gravity estimation by processing block 24. However, after the integration by block 28, the distortion primarily causes a monotonous component. This can be seen, for example, in the line labeled 62 in FIG. 4(d) where the integration has left an offset of about 0.25 $ms^{-1}$ in the velocity. If a linear filter is used at the gravity estimation stage, the errors in the estimated gravity due to the filter response spread cause significant velocity components (shown in the line labeled 52 in FIG. 4(d)).

Therefore, in accordance with the invention, the signal representing the vertical velocity is provided to a fourth processing block 30 which applies a filter to the vertical velocity signal to estimate the offset and any drift components present in that signal (step 111). The result of this filtering is a signal representing the fluctuations of the monotonous (i.e. offset and drift) component.

Traditional linear filters to obtain a DC (constant) or slowly changing (offset and drift) component include low-pass filter and moving average filters (which also exhibits low pass behavior). However, these filters affect adjacent samples through the time response corresponding to the filter. So, while an offset may be removed, a compensating "ghost offset" will appear before and after the corrected stretch of samples. These "ghost offsets" can significantly obscure the result of integrating the corrected stretch of samples to obtain a change in height.

Therefore, this problem is overcome by the processing block 30 preferably applying a non-linear filter to the vertical velocity signal to remove the offset and drift present in the signal (step 111).

In a preferred embodiment, the processing block 30 applies a median filter to the vertical velocity signal. As described above, the median filter effectively blocks pulses and oscillations in a signal while passing constant and edges (i.e. the offset and drift). A typical half window size for this filter can be 0.8 seconds (so the window encompasses 0.8 seconds worth of samples before the current sample and 0.8 seconds worth of samples after the current sample). In alternative preferred embodiments, the processing block 30 can apply a weighted median filter or a mode filter to the vertical velocity signal.

In a particularly preferred embodiment, the processing block 30 applies a median filter referred to herein as an 'adaptive median' filter. The adaptive median filter will be described in more detail below.

Figure 4D:
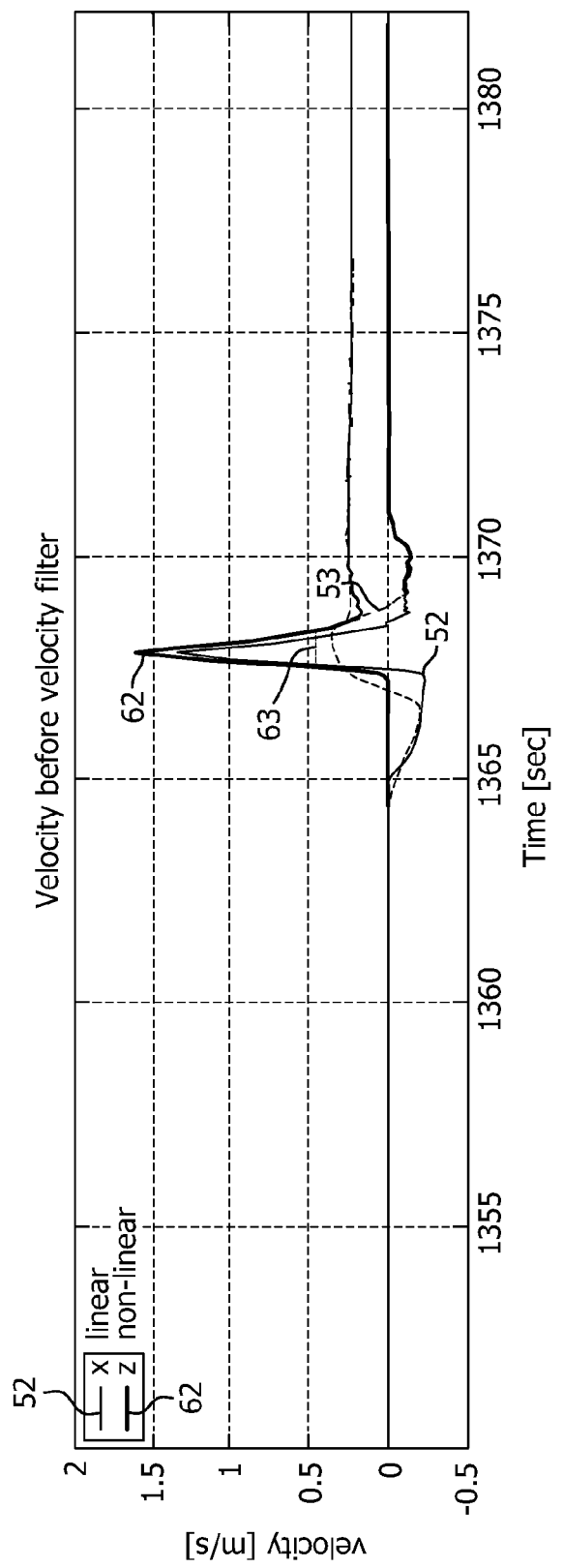
Figure 4E:
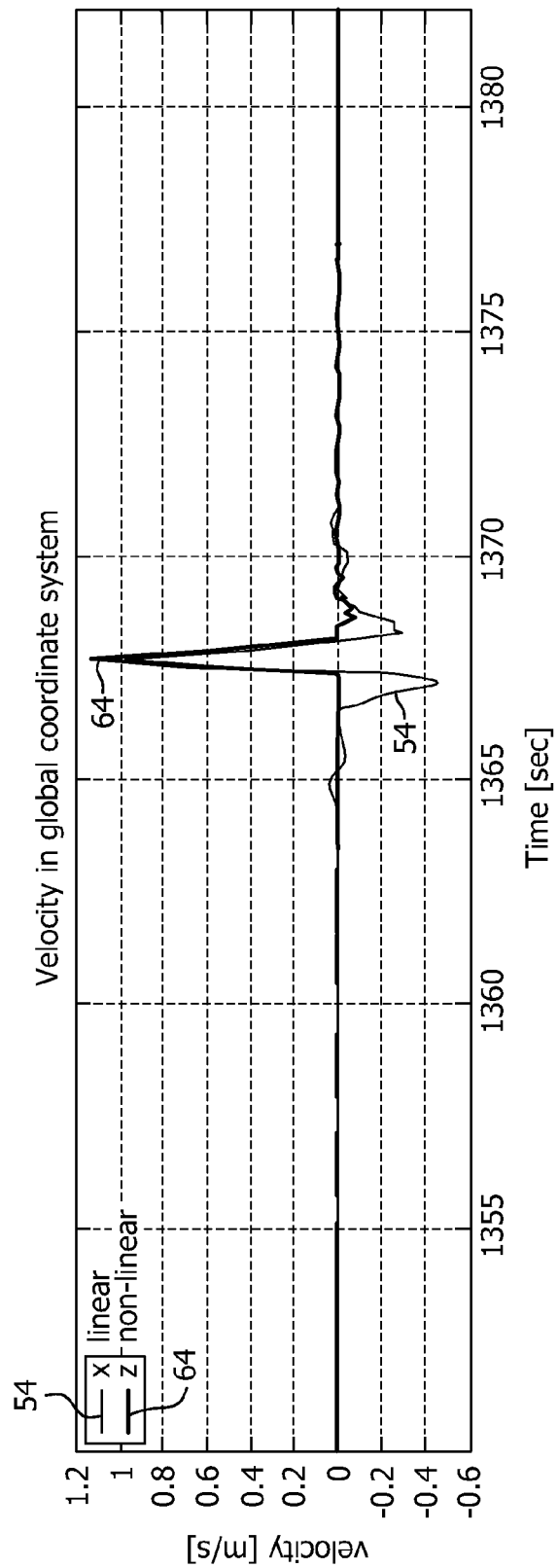

It will be appreciated that where the filter applied by processing block 24 is a non-linear filter, the fourth processing block 30 can apply a linear filter to the vertical velocity signal to estimate the offset and drift, depending on the application that uses the resulting velocity estimate. As can be seen in FIG. 4(d), the application of the non-linear filter in processing block 24 has limited the spread in the obtained velocity. The application of a linear filter to remove the offset and drift will cause some spread, but, in the context of that application, of an acceptably limited extent.

The signal representing the offset and drift in the vertical velocity signal that is obtained using a non-linear median filter and that is output of the processing block 30 is shown as dotted line 63 in FIG. 4(d). A signal representing offset and drift in the vertical velocity signal that is obtained using a linear moving average filter and that includes a 'ghost offset' as described above, is shown as dotted line 53 in FIG. 4(d).

This signal is input to an addition/subtraction block 32 along with the vertical velocity signal from integration block 28, where it is subtracted from the vertical velocity signal to give an offset and drift free vertical velocity signal (step 113). This signal is shown by line 64 in FIG. 4(e). Thus, the non-linear filter(s) applied during the earlier processing stages result in a more accurate estimate of the actual vertical velocity of the device 2. The equivalent vertical velocity obtained through the application of a linear moving average filter to the estimate of vertical velocity is shown by line 54 in FIG. 4(e), and it can be seen that part of the spread in the velocity has been removed, but a significant reversed component remains near the peak.

As with addition/subtraction block 26, the inputs to addition/subtraction block 32 may need to be synchronized to compensate for the delay introduced by processing block 30.

It will be appreciated that the non-linear median filter 30 that is applied to the vertical velocity signal and the subsequent addition/subtraction block 32 can be replaced by single filter, referred to herein as a 'complementary' median filter, which acts in the opposite way to the median filter, i.e. it passes the parts of the signal blocked by the median filter and blocks the parts of the signal passed by the median filter. Thus, the 'complementary' median filter passes the pulses of short duration representing the actual velocity of the device 2 and removes the offset and drift present in the vertical velocity signal.

The offset and drift free vertical velocity signal is then integrated with respect to time by processing block 34 to give the height or change in height of the device 2 (step 115). The initial position value $p(t_0)$ input to the integration block 34 will typically be unknown, but where the result of the integration is used to determine a change in the height, knowledge of the initial position is unnecessary. If it is desired to calculate the actual height, some calibration or initiation will be required in order to set $p(t_0)$.

Figure 4F:
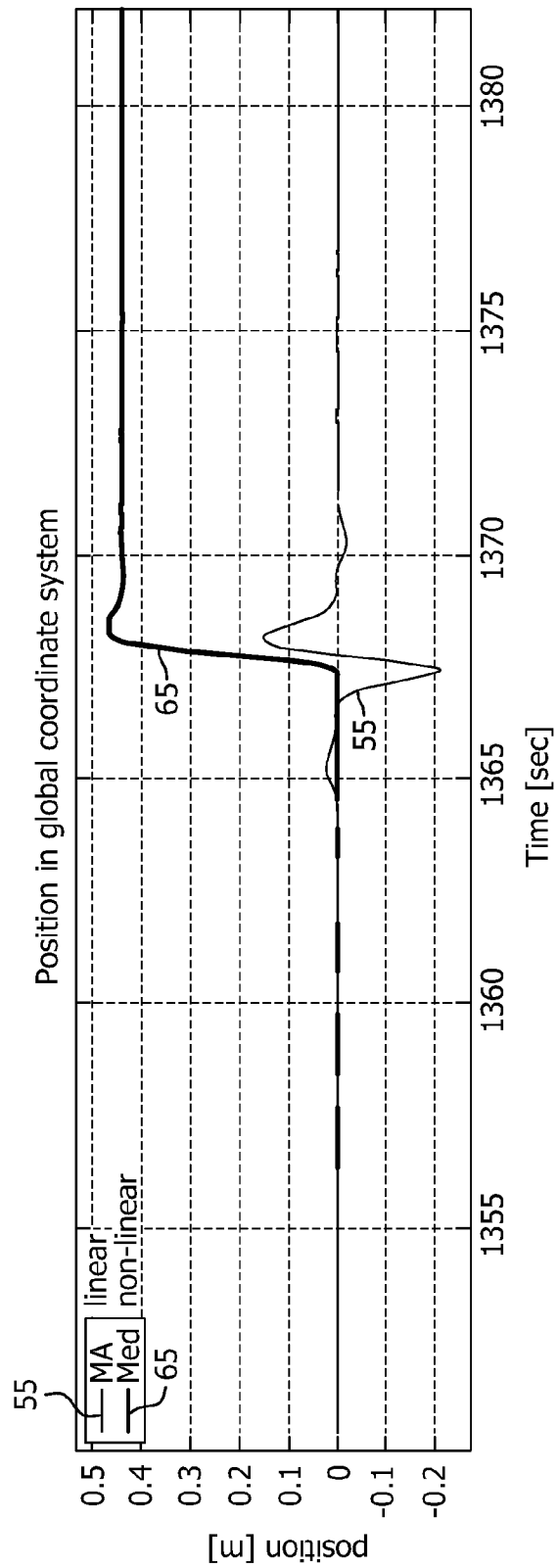

As suggested above, the device 2 is processing the accelerometer measurements in order to determine when there has been a change in height of the device 2 of a magnitude that corresponds to a fall by the user of the device 2. In addition, it will be appreciated that a change in height observed in the obtained height estimates that is indicative of a fall should be 'sustained', indicating that the device 2 is at a different height after the event than before. In other words, there should be a change in height from a first height before the fall to a second height (that is less than the first height) after the fall. Line 65 in FIG. 4(f) shows the position estimates obtained when non-linear filters are used during the processing, and indicates that a 'sustained' height change has occurred (although it will be noted that this figure indicates an increase in height rather than a fall). Line 55 in FIG. 4(f) shows the position estimates obtained when linear filters are used during the processing, and indicates that the erroneous velocity components that resulted from the filter response spreads compensate the rise completely, leaving effectively no (sustained) height change.

The output of integration block 34 provides the estimate of height. A change in height, as used to detect a fall or a rise (standing-up), results from computing the difference between the estimated heights at two time instants, for example at the current time instant and at a couple of (e.g. 2) seconds ago. There are multiple ways in which the change in height can be used in the decision logic for detecting a fall. For example, it can be determined whether the computed change in height exceeds a (downwards) threshold. A more sophisticated example would be to use the size of the change itself in a probability metric.

The change in height can be computed directly from the velocity estimates output by addition/subtraction block 32, bypassing integrator 34, by using a 'moving integrator' or summer that integrates (sums) between the time instants between which the height change is to be computed. The moving summer is similar to a moving average filter, except that the division (averaging) by the moving average filter's window length is omitted. So, basically, the velocity samples in the window are summed and returned as the output, where the window is the region between the two time instants. The preferred approach (integrate first and compute differences or compute moving sum) is down to consideration of computational load. The choice can be influenced by other factors, such as, for example, the number of window sizes over which the height difference is to be computed. The implementation of the moving summer can be optimized using similar techniques as known for MA filter implementations.

Figure 5:
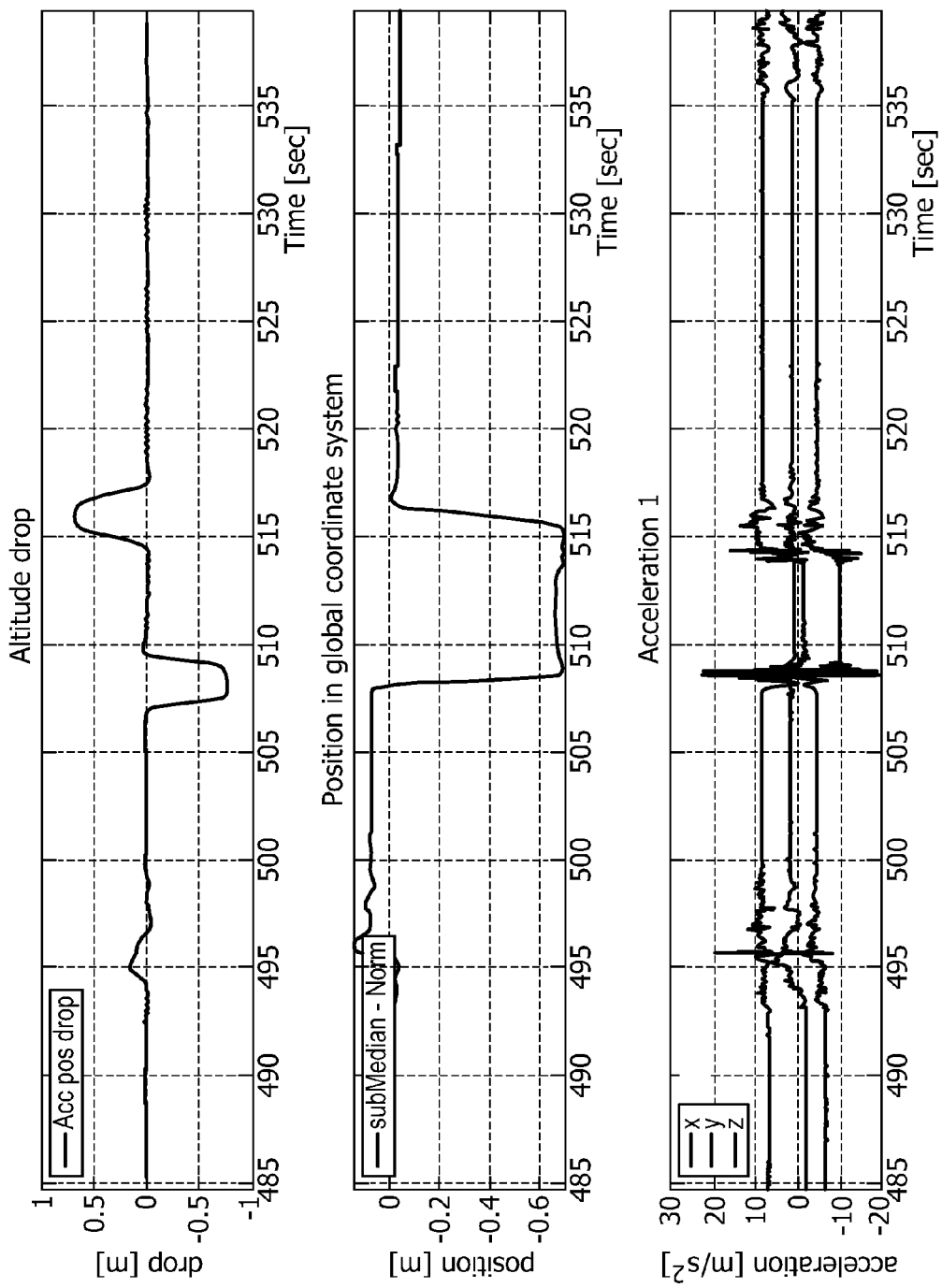
FIG. 5 is a set of graphs showing the change in height and height estimated from an exemplary set of acceleration measurements.

FIG. 5 shows the results of the processing according to the invention that is performed using a subMedian filter as the first filter 24 and a median filter as the second filter 30 on accelerometer measurements obtained during a fall. Thus, the graphs show the altitude drop (i.e. the change in height) and height (relative to an initial height of approximately zero) derived from the accelerometer measurements shown in the bottom graph. The height difference in the top graph is computed as the difference between the current height estimate and the height estimate a predetermined time period ago (in this example, the time period is 2 seconds). So, a drop in height results at the onset of the fall and remains visible for 2 seconds in the graph until the 'predetermined time period ago' passes the onset (i.e. 2 seconds later in this example).

Thus, in FIG. 5, there is a change in height indicative of a fall that occurs at around time t=509 (see top graph) and this change in height results in a sustained difference in the height of the device 2 (e.g. see the middle graph—the height of the device 2 observed in a time window before the change in height is higher than the height of the device 2 observed in a time window after the change in height.

As described above with reference to FIGS. 2 and 3, the acceleration acting in a vertical direction is estimated from the three-dimensional accelerometer measurements (for example by taking the norm of the accelerometer measurements) and then the filter is applied to the one-dimensional vertical acceleration estimate in order to estimate the acceleration due to gravity. However, in an alternative embodiment, the first filter can be applied to the signals from each of the measurement axes of the accelerometer 4 in order to estimate the acceleration due to gravity in three dimensions, prior to the estimation of the vertical component of acceleration. This three-dimensional gravity estimate can then be used to estimate the vertical component of acceleration in the three-dimensional accelerometer measurements, whereafter the gravity estimate (or another gravity estimate obtained using a further filter—the same or a different type to the first filter) is subtracted from the estimated vertical component to give the estimated vertical acceleration due to the motion of the device. In addition, using this approach the horizontal accelerations (due to motion) can be estimated and be processed in a similar manner to estimate horizontal velocity and displacement.

SubMedian Filter

As described above, in a preferred embodiment of the invention, a filter, termed herein as a 'subMedian' filter, is applied to the estimate of the vertical acceleration output by processing block 22 in order to estimate the gravity component in that signal. Alternatively, the subMedian filter can be used to estimate the three-dimensional acceleration due to gravity in the three-dimensional signals received from the accelerometer 4.

Also as indicated above, the gravitational component in the acceleration signal is more or less constant (i.e. DC), it changes direction in the accelerometer's frame of reference when the accelerometer 4 and device 2 are rotated, and the norm of the three-dimensional accelerometer measurements change when the accelerometer 4 is not perfectly calibrated.

Therefore, the filter applied to the accelerometer measurements (or the estimate of vertical acceleration) is required to output the DC component in the signal and to follow changes (for example due to rotations) instantaneously (i.e. no spread should be introduced as a result of applying the filter).

A low-pass filter is able to return the DC component, but introduces spread and doesn't quickly follow changes when the orientation of the accelerometer 4 changes. A median filter, although generally providing an acceptable output, can drift when the input signal is more complex (for example, a gentle but continuous movement of the accelerometer 4 up and down over a short height difference, followed by a large height change and a continuation of the short up and down movement, may reveal a drift in the output representing the estimated gravity component).

Figure 6:
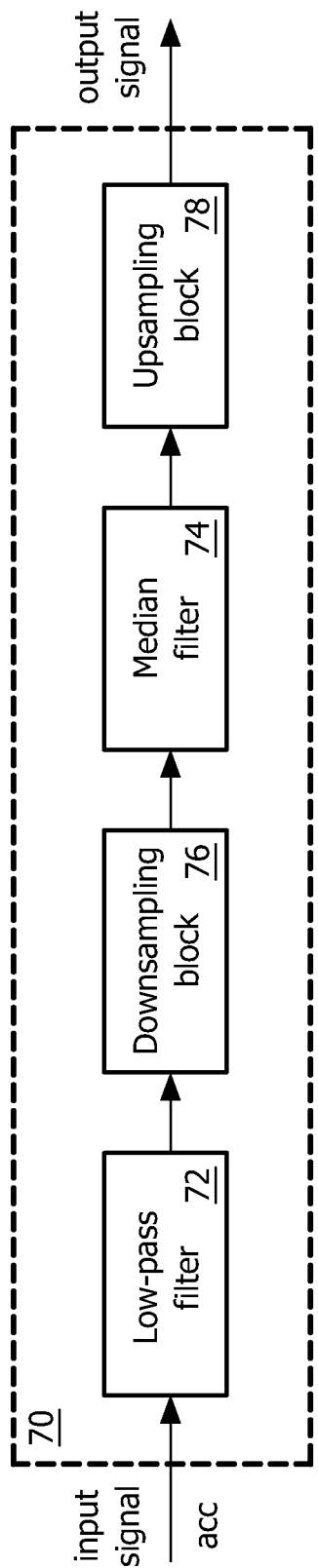
FIG. 6 is a block diagram of a subMedian filter used in preferred embodiments of the invention.

Therefore, a subMedian filter has been designed that combines a low-pass filter and a non-linear filter. Preferably this filter is a median filter or a median-based variant. An exemplary subMedian filter 70 is shown in FIG. 6.

Thus, a signal is input to a low-pass filter 72, and the low-pass filtered signal is input to a median filter 74. The low-pass filter 72 can have a larger bandwidth than when used alone, which allows the removal of some of the high frequency components in the input signal, but still allows quick movements to be followed.

The median filter 74 can alternatively be a median variant, such as a recursive median filter or a weighted median filter.

Since the input signal is low-pass filtered, according to the Nyquist-Shannon sampling theorem the low-pass filtered signal can be downsampled to the Nyquist rate corresponding to the bandwidth of the low-pass filter without aliasing effects. Downsampling to the Nyquist rate allows the operation of the median filter 74 to be more effective in two ways. On the one hand it provides a computational gain, since fewer samples are in the filter's window. On the other hand, it is realized that the filter should be more effective in removing the unwanted components (spikes). This will be further explained below, referring to FIG. 7.

Thus, the subMedian filter 70 further comprises a downsampling block 76 between the low-pass filter 72 and median filter 74 that downsamples the low-pass filtered signal to the Nyquist rate (i.e. twice the cut-off frequency of the low-pass filter 72). A parameter, termed the 'sub-sampling ratio' or 'subRatio' herein, determines the amount by which the sample rate of the low-pass filtered signal is reduced. A typical value for the subRatio is 20. The cut-off frequency for the low-pass filter 72 is typically set less than the bandwidth of the signal at the sub-sampled rate (the bandwidth being half the sampling rate). The bandwidth of the signal at the sub-sampled rate can, for example, be multiplied by 0.8 to set the cut-off frequency for the low-pass filter 72; the value of 0.8 being chosen to prevent aliasing effects upon downsampling. Thus, for a signal having a sampling rate of 50 Hz, the cut-off frequency for the low-pass filter 72 will typically be 1 Hz, being 0.8 times half the sampling rate after downsampling (which is 1.25 Hz).

An upsampling block 78 is provided to upsample the output of the median filter 74 back to the sampling rate of the signal input to the subMedian filter 70. As known in the art, the upsampling is followed by an interpolation filter, not shown in the figure, which is typically a low-pass filter of the same bandwidth as that one used in block 72. The filters should be scaled to keep signal strength at identical level. Upsampling can be performed in several ways, as is known in the art. For example, one way is to insert additional samples of zero value. Another example is to use sample & hold, i.e. to insert samples of the same value as the last available sample.

Applying the median filter 74 to a downsampled low-pass filtered signal makes the median filter 74 more effective in removing a spike in the signal (i.e. the accelerations due to motion of an accelerometer 4).

Figure 7:
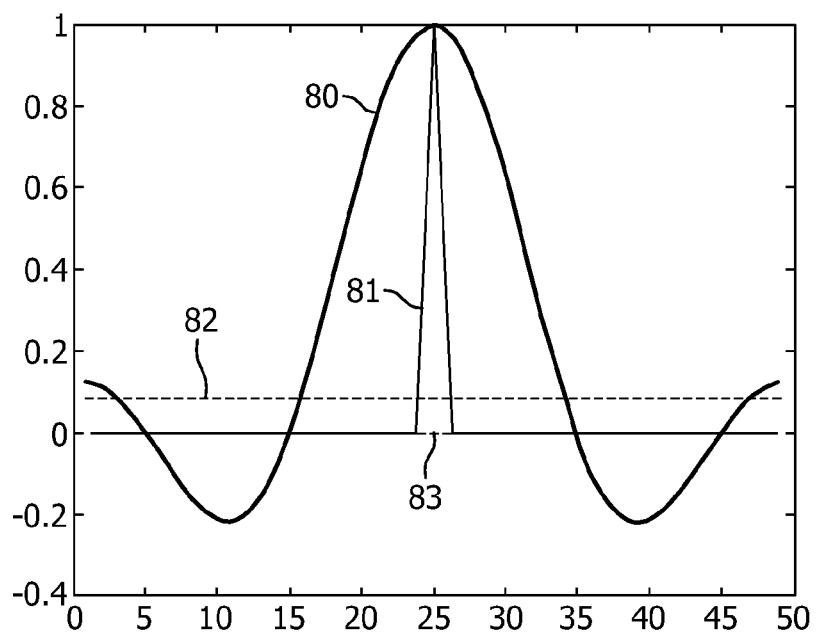
FIG. 7 is a graph illustrating a basic principle of operation of the subMedian filter.

FIG. 7 is a graph illustrating the basic principle of operation of the subMedian filter 70. Line 80 in FIG. 7 is a sinc signal corresponding to the bandwidth of the low-pass filter 72. Line 81 is the same sinc signal but sampled at the Nyquist rate, i.e. at the output of block 76. It can be seen that the subsampling is precisely at the zero crossings of the sinc signal 81 and therefore a pulse results in the signal.

Dashed lines 82 and 83 show the median-filtered value of signals 80 and 81 respectively. Thus, it can be seen that applying the median filter 74 to the subsampled low-pass filtered signal results in a better outcome (the true DC value).

Figure 8:
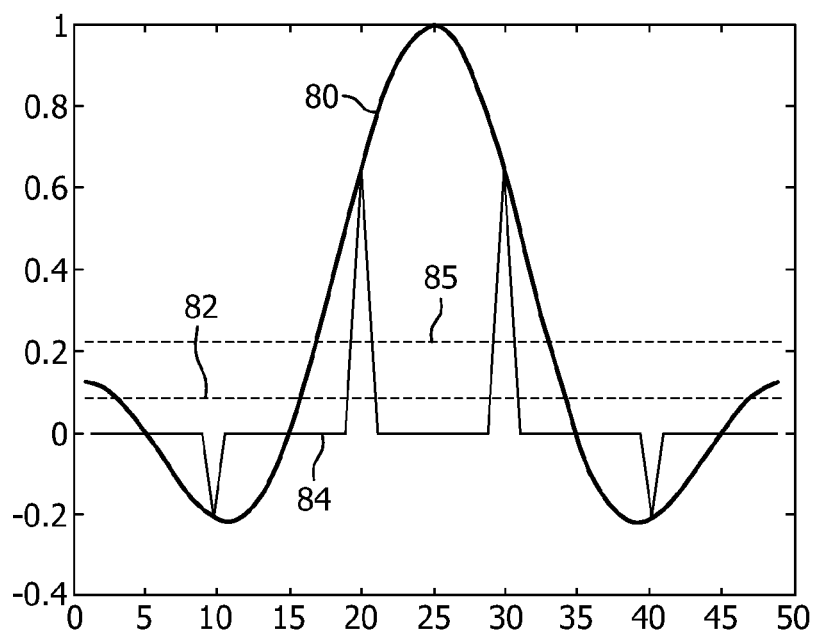
FIG. 8 is another graph illustrating the operation of the subMedian filter.

However, it will be appreciated that when sub- or downsampling the low-pass filtered signal, the choice of the first sample is arbitrary. FIG. 7 shows the ideal case where the subsampling is precisely at the zero crossings of the sinc signal 80. However, FIG. 8 illustrates the scenario where the sub-sampling results in samples halfway between the zero-crossings of the sinc signal (which is the worst case). Line 84 corresponds to the subsampled signal and dashed line 85 shows the median filtered signal.

Therefore the subMedian filter 70 can be adapted for this phase effect in the subsampled low-pass filtered signal. In particular, the downsampling block 76 can be configured to subsample at all phases, with the median filter 74 being applied to each subsampled signal. The final output of the median filter 74 can be a combination of the outcomes of the median filtering on each of the subsampled signals.

Figure 9:
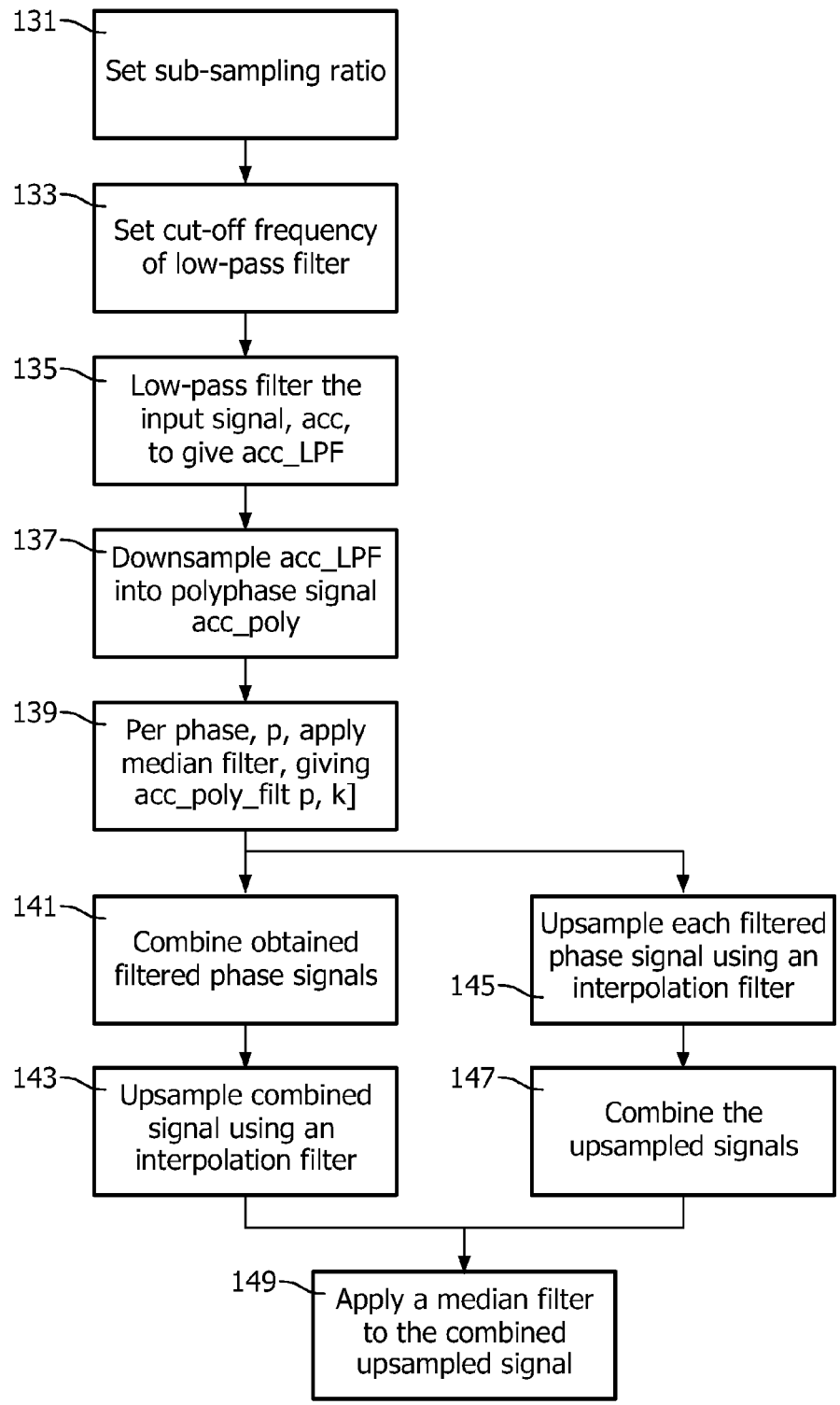
FIG. 9 is a flow chart illustrating an exemplary method of operating the subMedian filter.

FIG. 9 is a flow chart illustrating the operation of an exemplary subMedian filter 70. In step 131, the sub-sampling ratio, subRatio, is set, which can typically be 20 when the accelerometer signal is sampled at 50 Hz.

In step 133, the cut-off frequency of the low-pass filter 72 is set at 0.8 of Fs/2/subRatio (where Fs/2 is the full bandwidth of the signal, labeled 'acc' at the input of low-pass filter 72).

In step 135, the low-pass filter 72 is applied to the input accelerometer signal, acc, to give acc_LPF.

In step 137, the low-pass filtered accelerometer signal, acc_LPF, is downsampled into polyphase signal acc_poly according to the sub-sampling ratio. The number of ways acc_LPF can be subsampled is equal to the sub-sampling ratio. Hence, for each phase p, ranging from 0 to subRatio −1, the samples acc_poly at index k result as $$acc\_poly[p,k]=acc\_LPF[p+subRatio*k] \quad (1)$$

In step 139, the median filter 74 is applied to the downsampled signal for each phase, p. This gives a set of signals denoted acc_poly_filt[p,k]. In this example, the half window size of the median filter 74 is 1.6 seconds, although it will be appreciated that other values can be used.

Alternatively, as indicated above, other forms of median filters can be used, such as recursive median filters, or it is possible to iterate the (median) filter process (i.e. by repeating the median filtering several times on the outcome of the previous round).

Then, in step 141, each of the obtained filtered phase signals is combined into a single signal. The combination of the signals can be effected by taking the mean or median of each sample k over the subRatio number of phases, but other ways, e.g. based on other decision criteria, will be evident to those skilled in the art.

The combined signal can then be upsampled back to the original sampling rate (step 143).

In an alternative approach to steps 141 and 143, each of the filtered phase signals acc_poly_filt[p,k] obtained in step 139 can be upsampled back to the original sampling rate to give acc_poly_filt_up[p,t] first (step 145) and then the upsampled signals can be combined (step 147). This approach has the benefit that the signals acc_poly_filt_up [p,t] can include the phase, and their combining accounts for the phase, i.e. for the integer t such that t=p+subRatio*k, acc_poly_filt_up[p,t] is set to acc_poly_filt[p,k]. The remaining samples are found using an interpolation filter (the same as the low-pass filter applied before the downsampling step; preferably, the remaining samples are set to the neighboring assigned sample with "integer t", i.e. using a sample-and-hold scheme).

After step 143 or 149, a further median filter can be applied to the combined upsampled signal in order to remove any 'ringing' effects introduced by the interpolation filter. This median filter can have the same window size in seconds as the median filter applied in step 139.

It will be appreciated that not all steps are mandatory. The core of the subMedian filter is the application of the non-linear filter at a downsampled rate. The anti-aliasing filter, as well as accounting for the different phases, are refinements that can be applied depending on the application at hand.

Figure 10:
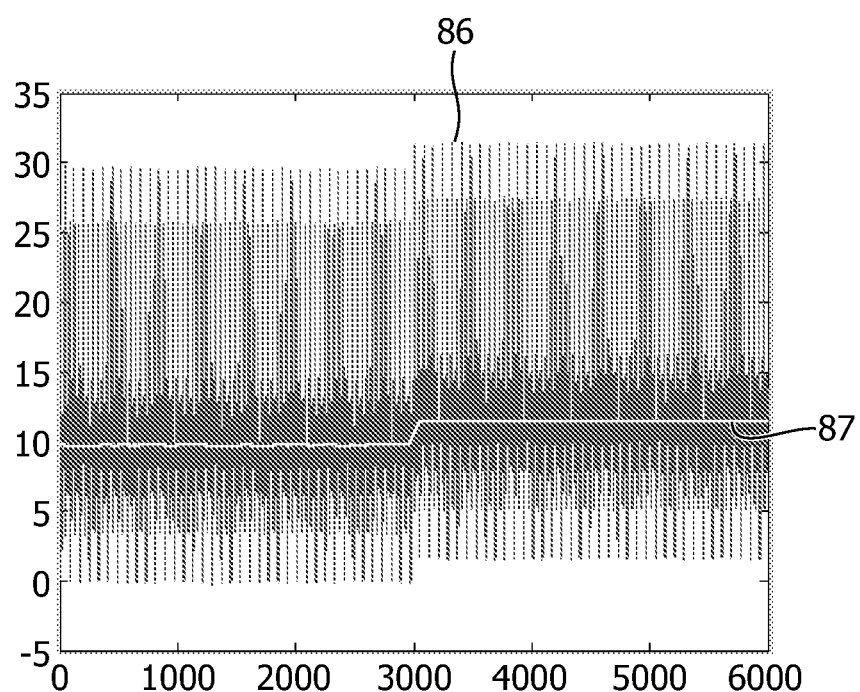
FIG. 10 is a graph illustrating the result of applying a subMedian filter to a signal comprising a set of sinusoidal signals and Gaussian noise.

FIG. 10 is a graph illustrating the result of applying a subMedian filter to a signal 86 comprising a set of four sinusoidal signals having different frequencies, phases and amplitudes and Gaussian noise. Furthermore, there is a step in the signal at time t=3000. Line 87 shows the result of applying a subMedian filter 70 as described above to signal 86, and it can be seen that the output provides a good estimate of the DC component and adequately tracks the step.

Adaptive Median Filter

As described above, in a preferred embodiment of the invention, a filter, termed herein as an 'adaptive median' filter, is applied to the estimate of the vertical velocity output by integration block 28 in order to estimate the offset and drift in that signal.

The purpose of the filter is to extract the velocity component in the velocity estimate that corresponds to the pulse form that deviates from a drifting DC (i.e. offset and drift) component. The offset may change and there may also be some drift.

During such a change, it is desirable to keep the current value for the offset, since it has been found that following the change in offset tends to follow the actual velocity signal and therefore leads to an underestimate in the actual velocity.

Therefore, in the adaptive median filter, the window size used to determine the median for a particular sample is adapted depending on the rank order of the median value in subwindows within the window. The rank order between the median values indicates whether there is an increase or decrease in the offset, and the subsequent adaptation (namely the choice of window size) aims to compensate for or prevent the underestimation in the value of the offset.

Figure 11:
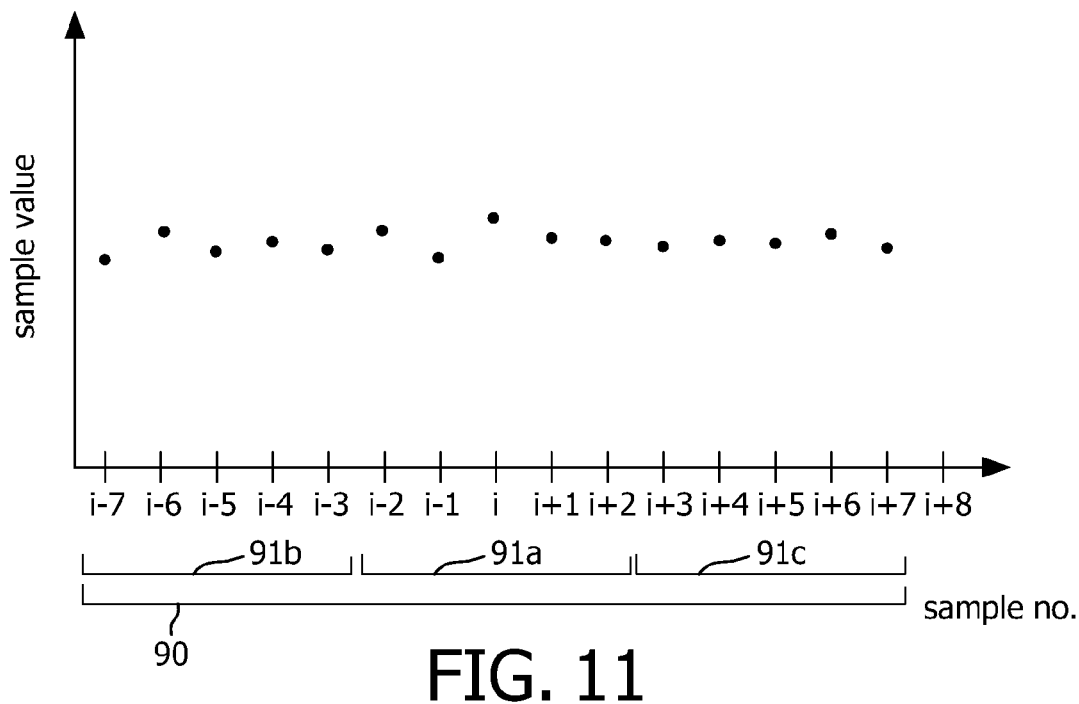
FIG. 11 is a graph illustrating the median filter subwindows used by an adaptive median filter used in preferred embodiments of the invention.

FIG. 11 shows part of a signal comprising 16 samples and a median filter window 90 centered on the current sample i with a half-window size of 7. In the adaptive median filter, the median filter window 90 is divided into three subwindows 91a, 91b and 91c (with a half-window size of 2 in this example). One subwindow (91a in FIG. 11) is centered on the current sample i, another subwindow (91b in FIG. 11) is centered on sample i−5 (i.e. the current sample minus the full subwindow width), and the third subwindow (91c in FIG. 11) is centered on sample i+5 (i.e. the current sample plus the full subwindow width).

As indicated above, the median value is calculated for each of the three subwindows and the three median values are ranked. The order of the ranking is used to determine the choice of window to use in producing the output of the adaptive median filter.

According to one exemplary embodiment, the rule set used to determine the choice of window for calculating the output is as follows:

- if the median value of the centre subwindow 91a is the maximum of the three median values, the output of the adaptive median filter is the median value in a subwindow having a half-window size that is larger than (e.g. twice) that of subwindow 91a and that is centered on sample i;
- if the median value of the centre subwindow 91a is between the values for the other subwindows 91b and 91c, the output of the adaptive median filter is the median value over a subwindow corresponding to the centre subwindow 91a and the subwindow 91b or 91c that generated the highest median value; and
- if the median value of the centre subwindow 91a is the minimum of the three median values, the output of the adaptive median filter is the median value obtained using the centre subwindow 91a.

According to another, preferred, embodiment, the rule set used to determine the choice of window for calculating the output is as follows:

- if the median value of the centre subwindow 91a is the maximum or minimum of the three median values, the output of the adaptive median filter is the median value in a subwindow having a half-window size that is larger than that of subwindow 91a and that is centered on sample i;
- otherwise, the output of the adaptive median filter is the value used for the previous sample (i.e. i−1).

In one implementation, where the median value of the centre subwindow 91a is the maximum or minimum of the three median values, a half-window size that is twice that of subwindow 91a is used to generate the output value. It will be appreciated, however, that other sized windows, larger than that of subwindow 91a, may be used.

Alternative actions to the use of the value for the previous sample where the median value of the centre subwindow 91a is not the maximum or minimum of the three median values can include using the value from the current centre subwindow 91a, or applying a recursive median filter to the current centre subwindow 91a or on the whole window.

In this way, the use of a larger window when the centre subwindow provides the maximum or minimum median value reduces the effect that the median filter follows a rising/falling trend of short duration present in the velocity signal. Using the previous value when the centre subwindow does not provide the maximum or minimum median value provides the constancy discussed above.

Figure 12:
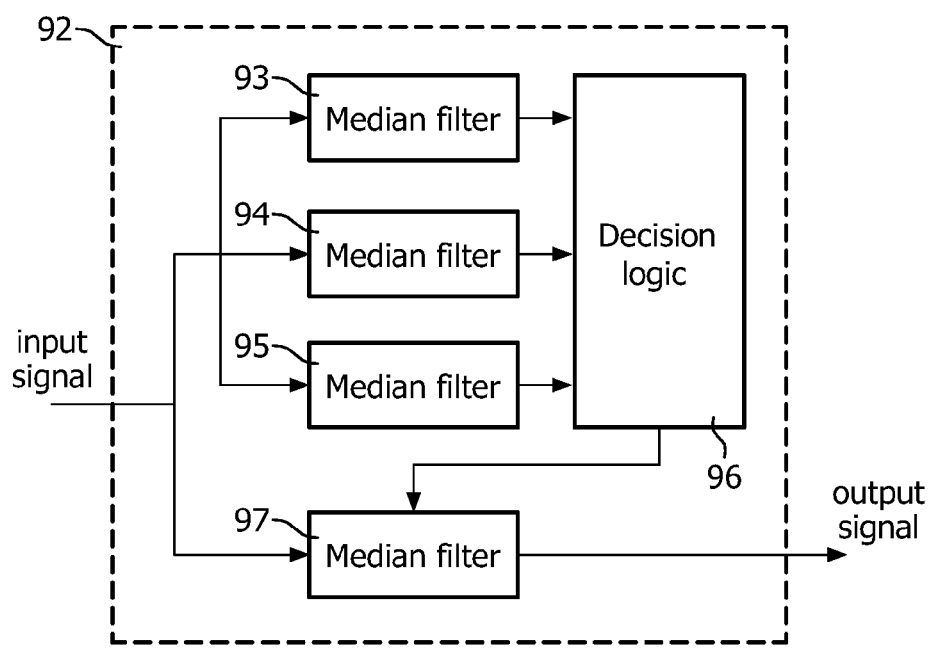
FIG. 12 is a block diagram of an exemplary adaptive median filter used in preferred embodiments of the invention.

FIG. 12 is a block diagram of an exemplary adaptive median filter 92 used in embodiments of the invention.

The input signal is provided to three filters, labeled 93, 94 and 95, which apply a respective one of the three subwindows 91a, 91b and 91c discussed above. In this embodiment, the filters are median filters, but it will be appreciated that the filters can be variants of a normal median filter. The output of each of these median filters is provided to decision logic 96 which implements one of the rule sets described above and determines the window size to be used to generate the output of the adaptive median filter 92.

A control signal indicating the required window size is output by the decision logic 96 to a median filter 97. Median filter 97 also receives the input signal (with a suitable delay to allow for the processing delay introduced by median filters 93, 94 and 95 and the decision logic 96) and operates on the input signal using the required window size. The output of median filter 97 is the output of the adaptive median filter.

It will be appreciated by those skilled in the art that the adaptive median filter 92 can be implemented using an alternative arrangement of components to that shown in FIG. 12. For example, as the rule set may provide that the median value of the centre subwindow 91a can be used as the output, the decision logic 96 may simply output this value rather than require median filter 97 recalculate it. Also, as is clear, reusing the previously computed output value doesn't require the full recomputation by the median filter 97.

In addition, it will be appreciated that it is possible for the window to be divided into more than three subwindows, as required, and it is also possible for the subwindows to have different sizes.

There is therefore provided an improved method and apparatus for estimating the velocity of a device in a horizontal or vertical direction based on measurements of the acceleration experienced by the device that overcomes the problems with the known techniques.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining an estimate of the velocity of a fall detection device in a horizontal or vertical direction, the method comprising:
    obtaining with an accelerometer of the device acceleration measurements of an acceleration acting on the device in three dimensions;
    using, by a processor of the device, a first filter and the obtained acceleration measurements to estimate acceleration due to gravity;
    estimating with the processor the acceleration acting in a horizontal or vertical direction due to motion of the device using the estimated acceleration due to gravity;
    integrating with the processor the estimate of the acceleration acting in said direction due to motion of the device to give an estimate of the velocity in said direction; and
    using, by the processor, a second filter to remove offset and/or drift from the velocity to give a filtered velocity;
    wherein at least one of the first filter and second filter is a non-linear filter.

2. A method as claimed in claim 1, wherein the step of using a first filter and the obtained measurements to estimate acceleration due to gravity comprises:
    estimating the acceleration acting in a vertical direction on the device from the obtained measurements; and
    applying the first filter to the estimate of the acceleration acting in a vertical direction to estimate the acceleration due to gravity;
    wherein the step of estimating the acceleration comprises estimating the acceleration acting in a vertical direction due to motion of the device; and wherein the step of estimating the acceleration acting in a vertical direction due to motion of the device using the estimated acceleration due to gravity comprises:
    subtracting the estimated acceleration due to gravity from the estimated acceleration acting in a vertical direction to give the estimate of the acceleration acting in a vertical direction due to motion of the device.

3. A method as claimed in claim 1, wherein the step of using a first filter and the obtained measurements to estimate acceleration due to gravity comprises:
    applying the first filter to the obtained measurements to estimate the acceleration due to gravity in three dimensions;
    and wherein the step of estimating the acceleration acting in a horizontal or vertical direction due to motion of the device using the estimated acceleration due to gravity comprises:
    using the estimated acceleration due to gravity to estimate the acceleration acting in a horizontal or vertical direction from the obtained measurements;
    and wherein when the acceleration acting in vertical direction due to motion of the device is estimated, the step of estimating the acceleration acting in a vertical direction due to motion of the device using the estimated acceleration due to gravity further comprises:
    subtracting the estimated acceleration due to gravity from the estimated acceleration acting in the vertical direction to give the estimate of the acceleration acting in the vertical direction due to motion of the device.

4. A method as claimed in claim 1, wherein the operation of the first filter comprises:
    downsampling an input signal; and
    applying a non-linear filter to the downsampled signal.

5. A method as claimed in claim 4, wherein the step of downsampling comprises generating a plurality of downsampled signals, each having a respective phase; and wherein the step of applying the non-linear filter comprises applying the non-linear filter to each of the plurality of downsampled signals.

6. A method as claimed in claim 5, wherein the operation of the first filter further comprises:
    combining the plurality of filtered signals into a single signal; and
    upsampling the single signal to the original sampling rate.

7. A method as claimed in claim 5, wherein the operation of the first filter further comprises:
    upsampling each of the plurality of filtered signals; and
    combining the plurality of upsampled filtered signals into a single signal.

8. A method as claimed in claim 4, wherein the operation of the first filter further comprises:
    prior to the step of downsampling, applying a low-pass filter to the input signal to produce a low-pass filtered signal; wherein the step of downsampling comprises downsampling the low-pass filtered signal to a rate based on the cut-off frequency of the low-pass filter.

9. A method as claimed in claim 1, wherein the operation of the second filter comprises:
    computing the median value in each of a plurality of subwindows centered at or near a sample of interest in an input signal; and
    adapting the window size of a median filter used to generate an output value for the sample of interest based on the computed median values, wherein the window size that is used to generate the output value is larger than that of the subwindow centered on the sample of interest if the median value of the subwindow centered on the sample of interest is the maximum or minimum of the plurality of median values.

10. A method as claimed in claim 1, wherein the non-linear filter is selected from a median filter, a weighted median filter, a recursive median filter and a mode filter.

11. A method as claimed in claim 1, further comprising the step of:
    estimating the position or height of the device by integrating the filtered velocity; or
    estimating the horizontal displacement or change in height of the device by summing the filtered velocity estimates in a time window over which the displacement or change in height is to be calculated.

12. An apparatus, comprising:
    processing means that are configured to:
        receive measurements of an acceleration acting on a device in three-dimensions from acquired with an accelerometer of the apparatus;
        use, with a processor of the apparatus, a first filter and the measurements of the acceleration to estimate acceleration due to gravity;

estimate with the processor the acceleration acting in a horizontal or vertical direction due to motion of the device using the estimated acceleration due to gravity;

integrate with the processor the estimate of the acceleration acting in said direction due to motion of the device to give an estimate of velocity in said direction; and use, with the processor, a second filter to remove offset and/or drift from the velocity to give a filtered velocity;

wherein at least one of the first filter and second filter used by the processing means is a non-linear filter.

13. A device that is configured to be worn by a user, the device comprising:

an accelerometer that measures the acceleration acting on the device in three-dimensions; and an apparatus as claimed in claim 12.

14. A system, comprising:

a device that is configured to be worn by a user, the device comprising an accelerometer that measures the acceleration acting on the device in three-dimensions; and a base unit that is configured to communicate with the device, and that comprises an apparatus as claimed in claim 12.

15. A computer program product, comprising a computer readable medium having computer program code embodied therein, the computer program code being configured such that, upon execution by a computer or processor, the computer or processor performs the method as claimed in claim 1.

* * * * *